US006876930B2

(12) United States Patent
Murray et al.

(10) Patent No.: US 6,876,930 B2
(45) Date of Patent: Apr. 5, 2005

(54) AUTOMATED PATHWAY RECOGNITION SYSTEM

(75) Inventors: Joseph Murray, Berkeley, CA (US); Donna Hendrix, Berkeley, CA (US); Daniel J Chin, Foster City, CA (US)

(73) Assignee: AGY Therapeutics, Inc., South San Francisco, CA (US)

( * ) Notice: Subject to any disclaimer, the term of this patent is extended or adjusted under 35 U.S.C. 154(b) by 244 days.

(21) Appl. No.: 10/090,698

(22) Filed: Mar. 4, 2002

(65) Prior Publication Data

US 2002/0168664 A1 Nov. 14, 2002

(51) Int. Cl.[7] .......................... G01N 31/00; G01N 33/48
(52) U.S. Cl. .......................................... 702/19; 702/27
(58) Field of Search ........................ 702/19, 27; 435/6; 536/23.1, 24.3; 706/45, 47; 712/200

(56) References Cited

U.S. PATENT DOCUMENTS

| 5,390,282 | A | * | 2/1995 | Koza et al. ................... 706/13 |
| 5,593,839 | A | | 1/1997 | Hubbell et al. |
| 5,807,522 | A | | 9/1998 | Brown et al. |
| 5,942,399 | A | | 8/1999 | Hillman et al. |
| 5,966,712 | A | | 10/1999 | Sabatini et al. |
| 6,023,659 | A | | 2/2000 | Seilhamer et al. |
| 6,189,013 | B1 | | 2/2001 | Maslyn et al. |
| 6,470,277 | B1 | * | 10/2002 | Chin et al. ..................... 702/19 |
| 6,607,879 | B1 | * | 8/2003 | Cocks et al. .................... 435/6 |
| 2003/0054394 | A1 | * | 3/2003 | Chin et al. ...................... 435/6 |

FOREIGN PATENT DOCUMENTS

WO WO/9915626 4/1999

OTHER PUBLICATIONS

Andrade, et al. "Automatic extraction of keywords from scientific text: Application to the knowledge domain of protein families", Bioinformatics, (1998) vol. 14(7): 600–60.
Andrade, et al. "Automated extraction of information in molecular biology", FEBS, (2000) vol. 476: 12–17.
Becker, et al. "A graph layout algorithm for drawing metabolic pathways", Bioinformatics, (2001) vol. 17(5): 461–467.
Brown, et al. "Knowledge–based analysis of microarray gene expression data by using support vector machines", Proc. Natl. Acad. Sci. USA, (2000) vol. 97: 262–267.
Eisen, et al. "Cluster analysis and display of genome–wide expression patterns", Proc. Natl. Acad. Sci. USA, (1998) vol. 95: 14863–14868.
Friedman, et al. "Genies: A natural–language processing system for the extraction of molecular pathways from journal articles", Bioinformatics, (2001) vol. 17(Suppl. 1): S74–S82.
Fukuda, et al. "Toward information extraction: Identifying protein names from biological papers", Proc. of the Pacific Symposium on Biocomputing (1998): 707–719.

Fukuda, et al. "Knowledge representation of signal transduction", Bioinformatics, (2001) vol. 17(9): 829–837.
Hua et al., "Construction of a modular yeast two hybrid cDNA library from human EST clones for the human genome protein linkage map," Gene, 1998, vol. 215, No. 1, pp. 143–152.
Hishiki, et al. "Developing NLP tools for genome informatics: An information extraction perspective", Genome Informatics, (1998) vol. 9: 81–90.
Humphreys, et al. "Automatically extracting enzyme interaction and protein structure information from Biological Science journal articles", Proc. of the Symposium on Artificial Intelligence in Bioinformatics of the 2000 Convention of the Society for the Study of Artificial Intelligence and the Simulation of Behaviour, (2000) (AISB–00), Birmingham, UK: 17–20.
Ingram et al., "Developing mouse models of aging: a consideration of strain differences in age–related behavioral and neural parameters," Neuralbiology of Aging, 1999, vol. 20, No. 2, pp. 137–145.
Krauthammer, et al. "Using BLAST for identifying gene and protein names in journal articles", Gene, (2000) vol. 259: 245–252.
Marcotte, et al. "Mining literature for protein–protein interactions", Bioinformatics, (2001) vol. 17(4): 359–363.
Masys, et al. "Use of keyword hierarchies to interpret gene expression patterns", Bioinformatics, (2001) vol. 17(4): 319–326.
Mrowka. "A Java applet for visualizing protein–protein interaction", Bioinformatics, (2001) vol. 17(7): 669–670.
Nevill–Manning, Craig. G., "Highly Specific Protein Sequence Motifs for Genome Analysis", Colloquium Paper, Proc. Natl. Acad. Sci. USA, (1998), vol. 95, pp. 5865–5871.
Ng, et al. "Toward routine automatic pathway discovery from on–line scientific text abstracts", Genome Informatics, (1999) vol. 10:104–112.
Ono, et al. "Automated extraction of information on protein–protein interactions from the biological literature", Bioinformatics, (2001) vol. 17(2): 155–161.
Proux, et al. "Detecting gene symbols and names in biological texts: A first step toward pertinent information extraction", Genome Inf., vol. 9: 72–80 (1988).

(Continued)

Primary Examiner—Kenneth R. Horlick
Assistant Examiner—Young J. Kim
(74) Attorney, Agent, or Firm—Pamela J. Sherwood; James S. Keddie; Rebecca D. Taylor

(57) ABSTRACT

There is a pressing need for computer-implemented tools that can summarize and present the enormous amounts of public literature to facilitate analysis of gene expression data. The present invention provides techniques and systems for efficiently integrating public literature regarding gene function with data from gene expression profiling experiments. Information from literature databases relating to a particular set of DNA sequences of known expression pattern is retrieved, processed, cross-referenced and viewed to provide further information about a particular DNA sequence to facilitate its identification as a candidate gene.

17 Claims, 13 Drawing Sheets

OTHER PUBLICATIONS

Raychaudhuri, et al. "Basic microarray analysis: Grouping and feature reduction", *Trends in Biotechnology*, (2001) vol. 19(5): 189–193.

Raychaudhuri, et al. "Associating genes with gene ontology codes using a maximum entropy analysis of biomedical literature", *Genome Res.* (2002) vol. 12: 203–214.

Rindflesch, et al. "Mining molecular binding terminology from biomedical text", *Proc. AMIA Symposium*, (1999): 127–131.

Salamonsen, et al. "BioJAKE: A tool for the creation, visualization, and manipulation of metabolic pathways", *Proc. of the Pacific Symposium on Biocomputing 1999*, (1999).

Sekimizu, et al. "Identifying the interaction between genes and gene products based on frequently seen verbs in Medline abstracts", *Genome Inf.*, (1998) vol. 9: 62–71.

Schatz. "Information retrieval in digital libraries: Bringing search to the net", *Science*, (1997) vol. 275(5298): 327–334.

Stephens, et al. "Detecting gene relationhips from Medline abstracts", *Proc. of the Pacific Symposium on Biocomputing*, (2001): 483–495.

Tamayo, et al. "Interpreting patterns of gene expression with self–organizing maps: Methods and application to hematopoietic differentiation", *Proc. Natl. Acad. Sci. USA*, (1999) vol. 96: 2907–2912.

Thomas, et al. "Automatic extraction of protein interactions from scientific abstracts", *Proc. of the Pacific Symposium on Biocomputing*, (2000): 538–549.

Wong. "A protein interaction extraction system", *Proc. of the Pacific Symposium on Biocomputing 2001*, (2001): 1–11.

Yoshida, et al. "PNAD–CSS: A workbench for constructing a protein name abbreviation dictionary", *Bioinformatics*, (2000) vol. 16(2): 169–175.

* cited by examiner

AUTOMATED PATHWAY RECOGNITION SYSTEM

BACKGROUND OF THE INVENTION

The present invention relates to bioinformatics and its use in methods of characterizing and identifying candidate genes. More particularly, the invention relates to the use of information extraction in the analysis of data from high-throughout gene expression profiling experiments.

High-throughput gene expression profiling techniques, such as those employing DNA microarrays, have become a standard and widely used technique for the identification of drug targets, gene therapy targets and therapeutic protein targets in human medicine (see U.S. Pat. Nos. 5,807,522 and 5,593,839). The early and efficient identification of target genes, otherwise known as "candidate" genes, using these techniques could significantly reduce the overall costs and time taken to develop and market actual products.

The rise in popularity of gene expression profiling, coupled with the increase in complexity of the experiments, has led to a tremendous increase in the amount of information that has to be organized and processed. One experiment alone, for example a time course of a disease process or a comparison between a treated sample with a non-treated control, may provide data on several thousand different genes. Analyzing and storing this data in a meaningful way has become rate limiting for biologists.

Several computational tools have been applied to this problem. For example, computational methods have assigned names to DNA sequences by comparing their sequence with sequence of named genes in public databases using such algorithms as BLAST (see generally U.S. Pat. No. 6,023,659). DNA sequences have also been assembled and grouped into functional hierarchies by specific algorithms to help investigators interpret gene expression data (U.S. Pat. No. 6,023,659).

More recently, gene expression profiles have been examined using methods that can cross-compare the expression profiles of many thousands of genes across many different experiments (for example Eisen et al P.N.A.S. 95, 14863–8). These methods employ pattern recognition algorithms to cluster genes with a similar expression patterns facilitating the facile identification of groups of genes that are co-regulated. Both supervised and unsupervised pattern recognition algorithms can be used to for clustering. Supervised pattern recognition algorithms require a priori knowledge that forms a training set, whereas unsupervised pattern recognition algorithms do not need a priori knowledge and are typically used to discover latent patterns. Many unsupervised clustering methods have been applied to gene expression profile data: these include hierarchical, K-means, self-organizing maps (Tamayo et al. PNAS 96:2907–12), or support vector machines (M. Brown et al. PNAS 97:262–7).

Once gene expression data has been gathered and analyzed, mostly by computer, researchers typically spend a significant amount of time gathering information from public databases, in particular public literature databases, in order to annotate their genes of interest, increase their confidence in a particular result, and permit the discovery of candidate genes. These methods are typically manually performed, in part due to a lack of tools to organize and process the enormous amount of public literature that is available for many of these genes. Because of this manual step, the available methods do not allow the efficient and facile identification of candidate genes.

Thus, there is a pressing need for tools that can process, summarize and cross-reference the enormous amounts of public literature, and allow this data to be used in combination with gene expression profiles to aid in discovering candidate genes. Since public literature is making a transition from printed media to digital media in the form of literature databases, an opportunity has emerged for computers to assist in this effort. There have been several attempts to use information extraction (IE) and natural language processing (NLP) methods within the context of biology. For example, protein-protein interactions can be examined using IE approaches (Science. 1997,275(5298): 327–334; Proux (1988) Genome Inf. Workshop 9, 72–80; Hishiki et al, (1998) Genome Inf. Workshop 9, 81–90). However, IE and NLP have not yet been used in the context of examining gene expression profiling data to identify candidate genes.

Thus, within the art, there is a need for methods and techniques that can efficiently annotate genes with known information, in particular information from public literature databases regarding relationships between gene functions, and organize this information with gene expression profiles, facilitating the identification of candidate genes.

SUMMARY OF THE INVENTION

The present invention provides techniques and systems for facilitating identification of candidate genes from a plurality of DNA sequences. More particularly the invention uses computer-implemented methods and systems to efficiently extract and process information on gene pathways and gene relationships and combine this information with results of other analyses in order to facilitate the rapid analysis of gene expression data.

According to one embodiment, the present invention provides a method that integrates the enormous amount of public literature regarding gene function with data from gene expression profiling experiments. Information from literature databases relating to a particular set of DNA sequences is retrieved, and using information extraction methods the literature is processed. The data is then cross-referenced and viewed to provide further information about a particular DNA sequence to facilitate its identification as a candidate gene. This cross-referenced information may be stored in a database. Additional annotation can be added by a user to this database, and these comments may further facilitate the identification of candidate genes by altering the manner in which information is cross-referenced in future iterations of this process.

In another embodiment, the present invention provides a method for analyzing a group of genes identified through analysis of gene expression profiling experiments, wherein the groups of genes have been grouped together by a commonality in their gene expression patterns. Clustering algorithms may be employed to automatically group genes by their expression pattern and a cluster of genes may represent a group of genes. These clustering algorithms may be supervised or unsupervised. A further embodiment of the invention provides a method for using both supervised and unsupervised clustering algorithms to automatically group genes by their expression pattern. The gene expression data analyzed may be from microarray experiments.

In yet another embodiment, information may be extracted from one of many literature databases, for example MEDLINE, the U.S.P.T.O. and W.I.P.O. patent database, KEGG, OMIM or MIPS, etc, and can be ranked by quality, based on a citation index, where information from highly cited journals is of higher quality than information from lower cited journals. Information can be extracted from literature database using natural language processing algorithms. The extracted information can pertain to a pathway in which a gene functions, or information about interactions between different genes on a list.

In further embodiments, the invention provides a data processing system for identifying candidate genes where the system has instructions for accessing, extracting, cross-referencing and viewing information from a literature database pertaining to a gene with a known expression pattern. The system of the invention contains a processor, memory, and instructions for accessing, extracting, cross-referencing and viewing the information. The cross-referenced information may be stored in a database and readily accessed by a user.

In yet another embodiment, the data processing system contains instructions to access a biomedical journal literature database, and further instructions for ranking the biomedical publications using a citation index and associating the ranking score with the information extracted from the journal. The ranking of this information allows information extracted from a literature database to be given a significance score.

The invention also provides an integrated data processing system containing instructions for clustering genes based on expression pattern behavior and has instructions for accessing, extracting, cross-referencing and viewing information from a literature database pertaining to a gene or a group of genes that have similar behavioral pattern.

BRIEF DESCRIPTION OF THE DRAWINGS

Preferred embodiments according to the invention will be described with reference to the Figures, in which like reference numerals denote like elements and in which.

DETAILED DESCRIPTION OF THE PREFERRED EMBODIMENTS

Figure 1:
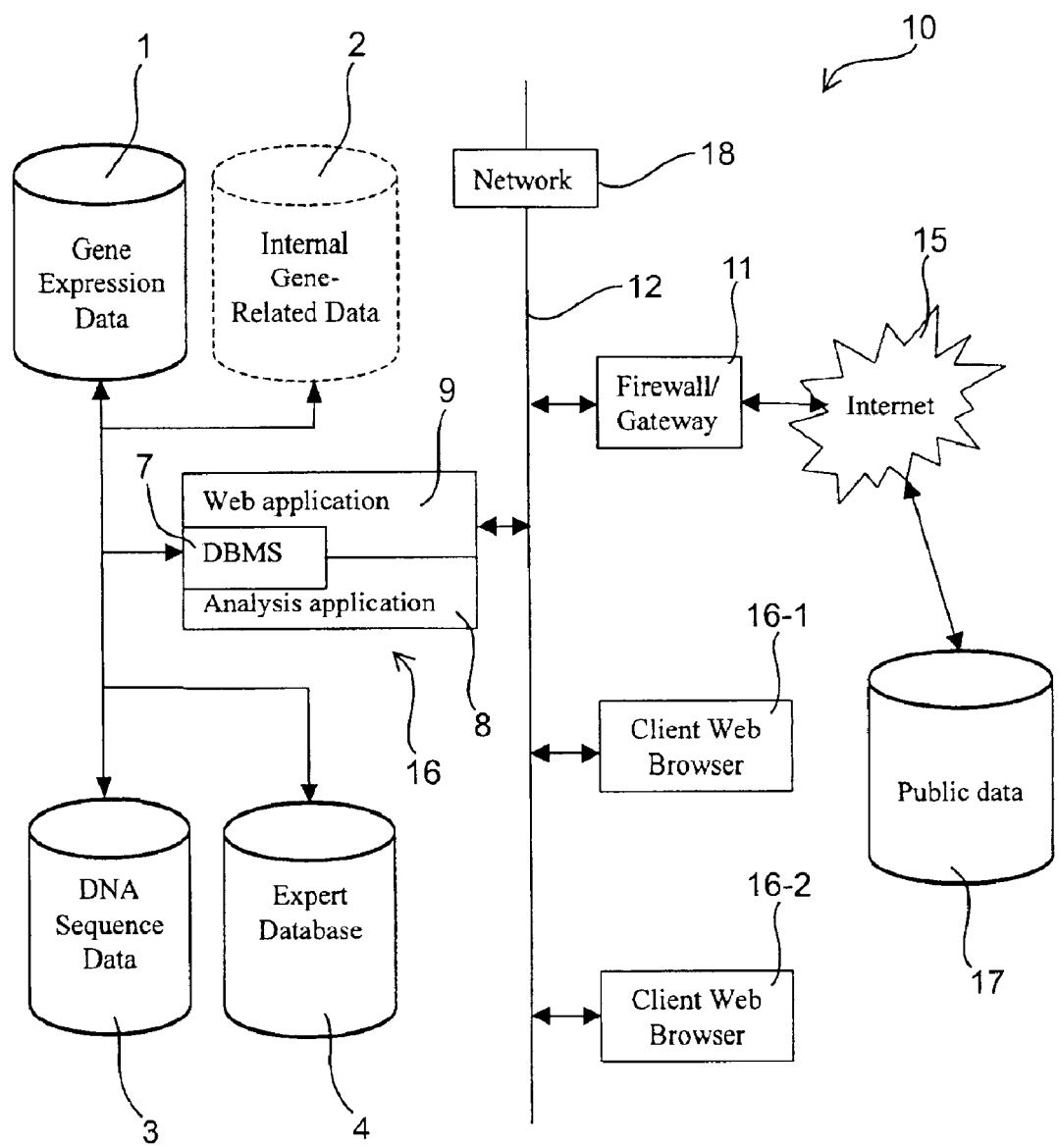
FIG. 1 is a simplified block diagram of a client server network for providing database services incorporating one embodiment of the invention.

The present invention provides an improved method for examining gene expression profile data for the discovery of candidate genes. The invention employs information extraction techniques such as natural language processing, and can be used to rapidly determine the relationships between different genes once gene expression profiling experiments have been performed on those genes. In a preferred embodiment, the genes are clustered by their expression patterns using data provided by microarray experiments. The automated information extraction provides relevant information about the relationships between individual genes in a group of genes that has undergone cluster analysis. In the following description, numerous specific details are set forth in order to provide a thorough understanding of the present invention. It will be apparent, however, that the present invention may be practiced without limitation to some of the specific details presented herein.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

This invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a", "and", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed. All publications mentioned herein are incorporated herein by reference to disclose and describe the methods and/or materials in connection with which the publications are cited.

The following terms are used throughout the specification. The description are provided to assist in understanding the specification, but do not necessarily limit the scope of the invention.

Database—A database can be any computer medium wherein data can be stored. A database can be relational or object-oriented, and can be a spreadsheet, a flat text file, a table or a list, for example.

Gene—A gene, in this context, includes any nucleic acid coding sequence or a gene product such as an mRNA or protein encoded by a gene.

DNA sequence database—This is a database containing information pertaining to DNA sequences. The information may be the sequence itself, a unique identifying name of the sequence, a name of the gene represented by the sequence, a function of the gene in terms of its enzymatic or other activity, its expression pattern, a pathway or physiology it is associated with, or any other information added by a user, or by any computer-assisted methods, which relates to the gene represented by the sequence.

Public literature database—This is a database, normally a publicly available database or a database that is commercially available, containing information about genes. The literature databases disclosed herein are the public MEDLINE database of the National Library of Medicine, as made available through PubMed, a database of full-text issued patents and published US and worldwide patent applications, such as the databases searchable through the world wide web at the U.S. Patent and Trademark Office (U.S.P.T.O.), or the World Intellectual Property Organization (W.I.P.O.), the Kyoto Encyclopedia of Genes and Genomes (KEGG) (Ogata et al, Nucleic Acids Res. (1999) 27:29–34), the Munich Information Center for Protein Sequences (MIPS) (Mewes et al, Nucleic Acids Res. (1999) 27:44–8), or the Online Mendelian Inheritance in Man (OMIM) database, although any database containing abstracts from periodicals, full-text articles, summaries of gene interactions, patent information or any other textual information about genes may suffice. In this context a text database is synonymous with a literature database.

Internal database—This is an internal database containing, for example information about gene expression patterns, sequences, annotation and literature etc. The internal database will normally contain information that has been generated through downloading or transferring information from any public literature database to a database within an internal network. Internal databases are typically maintained in confidentiality from the public through a firewall.

Gene expression database—A database containing information about the expression patterns of genes. Gene expression may be described e.g. as ratios, normalized ratios, absolute values or normalized values, etc. A gene expression pattern may be the result of performing gene expression profiling experiments. Gene expression profiling experiments can provide data on the expression patterns of up to several thousand genes in several different experimental and control samples. The gene expression database stores these patterns. The data are stored in a convenient format, such as a tab-delimited text file, for further analysis. The gene expression database also contains cluster information.

Cluster—A cluster is a group of genes e.g. that have some commonality in their expression pattern. For example, a cluster of genes may be a group of genes that are all up-regulated in a certain cell type that has been treated with a certain agent. A cluster can also be a group of genes that are up-regulated or down regulated by certain agents but not others. Clusters can be the result of cluster analysis of a gene expression data, derived from the gene expression database with supervised and/or unsupervised pattern recognition algorithms, such as hierarchical, K-means, self-organizing maps or support vector machines.

Supervised and unsupervised pattern recognition algorithms—Pattern recognition algorithms are either supervised or unsupervised. Supervised pattern recognition methods require a priori knowledge which forms a training set, and are applied towards categorizing data according to pre-defined groups. A simple Bayesian approach can be taken, or more sophisticated maximum entropy or nearest neighbor analysis may by preferred. Unsupervised methods encompass clustering and dimension reduction strategies, and clustering can be accomplished through self-organizing maps, K-means, or support vector machines clustering. Unsupervised methods may be used to discover patterns (for example, of gene expression) that only become apparent under certain physiological, developmental, transgenic, gene knock-out or drug-induced conditions whereas supervised methods may be used to discover genes with a particular expression profile. A combination of supervised and unsupervised pattern recognition algorithms may be used in the methods of this invention.

Information extraction (IE)—IE is a natural language processing (NLP) method for transferring knowledge from unstructured natural language data, for example a literature database such as MEDLINE, into a structured and summarized form that can be placed in another database for easy access and use. The major goal of information extraction within the scope of this invention is to discover the relationships between genes by searching literature for gene names, examining text phrases or sentences containing the gene names, and determining the relationship between the genes using information extraction. Information extraction will often employ NLP techniques, such as part-of-speech tagging, stemming, tokenization, stop word removal, multi-word (noun) phrase identification, template filling, Hidden Markov Models and anaphora detection.

Cross-referencing—The determination of the biological relationship between the functions of two or more genes. The biological relationship between genes may be simple, or complex. For example, genes whose products encode enzymes in the same biochemical pathway, or genes whose products physically interact, for example in a signal transduction pathway, have a simple relationship. When two different genes that are not related by any simple relationship or interaction show similar gene expression behaviors, they have a complex relationship. A relationship between two genes may also be inductive, as in one gene product may induce a second gene product. More complex relationships may exist between genes if the two genes both induce the same gene product. Relationships between genes can be said to be activating, binding, inhibiting, adhering inducing, transporting, exporting, creating, phosphorylating, de-phosphorylating, upstream of or downstream of, for example. A biological pathway can be constructed from cross-referenced information about relationships between genes.

Candidate gene—A candidate gene may trigger, prevent, ameliorate or affects a variety of diseases or physiological states. In a drug development process, potential drugs may be tested against products of candidate genes, and candidate genes may also be used to diagnose diseases or physiological states.

1) The Database Environment

FIG. 1 depicts a network system 10 suitable for storing and retrieving information in databases of the present invention. The network 18 includes a network cable 12 to which a server 14 and clients 16-1 and 16-2 (representative of possibly many more clients) are connected. The cable may be also connected to the internet 15 and public databases 17 through a firewall 11.

The network 18 may be any one of a number of conventional network systems, including a local area network (LAN) or a wide area network (WAN), as is known in the art. The network includes functionality for packaging client calls into a well known format, for example a URL, together with any parameter information into a format suitable for transmission across a cable or wire for delivery to server 14.

Server 14 includes hardware necessary for running software to access database data for processing user requests and provide an interface for serving information to client machines 16-1 and 16-2. In a preferred embodiment, the software running on the server machine supports the World Wide Web (web) protocol for providing page data between a web server 14 and a client 16-1 or 16-2. The web application 9 provides a user interface between server and a client. Server 14 receives information through the network to carry out instruction provided by a user, and requests are directed to the appropriate hardware and analysis applications 8. As may be necessary, the server may be distributed over two or more machines. A first server may be a web server running web applications 9 and the second server may be an analysis server running analysis applications 8. Optionally an analysis computational node can added to the network to provide for increased computational capacity. As shown, server 14 also includes a database management system, for example the Oracle Suite, or the IBM DB2 Discovery Link systems for managing, retrieving, organizing and accessing data.

Analysis application 8 includes executable code necessary for generation of database queries, for example, embedded SQL statements. In addition, analysis application 8 includes files which contain references, pointers and addresses to the various software entities that are contained within the server as well as the various data which must be accessed to service user requests.

Each of clients includes a web browser for providing a user interface to server. Through the web browser, clients construct requests for retrieving and processing data from public 17 or internal data, defined by 1, 2, 3, and 4. Thus, the user will typically type into a user interface, or point and click to user interface elements such as buttons, pull down menus; and the like, as typically employed in graphical user interfaces. The requests so formulated with the client's web browser are transmitted to web application 9 which transmits requests to the analysis application which formats and executes the instructions In the embodiment shown, analysis application constructs a query in database language, for example Sybase or Oracle SQL, and data in a database is accessed and relevant information extracted from the database typically through a database management system 7.

Web application 9 provides an appropriate graphical user interface, such as Hypertext Mark-up Language (HTML) browser to a client machines 16-1 and 16-2, are is employed by the user to formulate his or her requests. The web application 9 sends instructions for analysis, as determined by the request, to the analysis application 8. The analysis application 8 converts the request to an SQL query, which is used by database management system 7 to access relevant data in databases and provide that data to server 14 in an appropriate format. Server 14 then processes the data, stores said processed data in expert database 4 and generates a new HTML document relaying the processed data to the client as a view in user interface 16-1 and 16-2. While a server 14 and web browser is employed in FIG. 1, other communication systems will be suitable that do not rely on web applications 9.

When a network employs a server with web applications and clients, it should support a TCP IP protocol. Local networks such as this can be referred to as "intranets". An advantage of such intranets is that they allow easy communication with public domain databases residing on the World Wide Web, such as GenBank and MEDLINE. Thus, in an embodiment, clients can directly access data in public databases residing on the internet using an HTML interface provided by web browsers and web server. A firewall preserves the privacy of the gene expression data 1, sequence data 3, expert database 4 and other internal data 2.

In a preferred embodiment, DNA sequence data 3 is stored in a flat file database including partial or full-length nucleotide sequences of genes. Associated with this nucleotide sequence is other information about the nucleotide sequence, such as the gene name to which it corresponds, and the name of the gene product, e.g. enzyme that the gene encodes. The gene expression data is preferably stored in a database in a relational format, for example Oracle™ or Sybase database architectures can be used. The database(s) containing DNA sequence data 3, gene expression data 1, internal data and expert data 4 can be XML, relational or object-oriented, depending upon the requirements of the system. In a preferred embodiment, public data 17 is utilized. An internal database 2 of public data can be created by transferring information from a public database 17 to a private network.

Suitable dual or multi-processor server computer machines may be selected, for example, from any of the following: Sun Enterprise 450 or Sun Enterprise 3500, (Sun Microsystems, Inc. of Mountain View, Calif.), Compaq AlphaServer ES45 (Compaq Computer Corporation of Houston, Tex.), and IBM iSeries Model 820 (International Business Machines of White Plains, N.Y.). These server workstations may have an operating system e.g. Sun Solaris, Compaq Tru64, Linux, Unix-variants, etc. The client computer machines may be, for example, a Macintosh™ (Apple Computer Inc of Cupertino, Calif.), a PC, Unix workstation, etc. Workstations may be TCP/IP capable with a Netscape or Microsoft Internet Explorer Web Browser. The network may include a 10/100-base-T or greater connection, be TCP/IP capable, and provide access to the internet.

Figure 2:
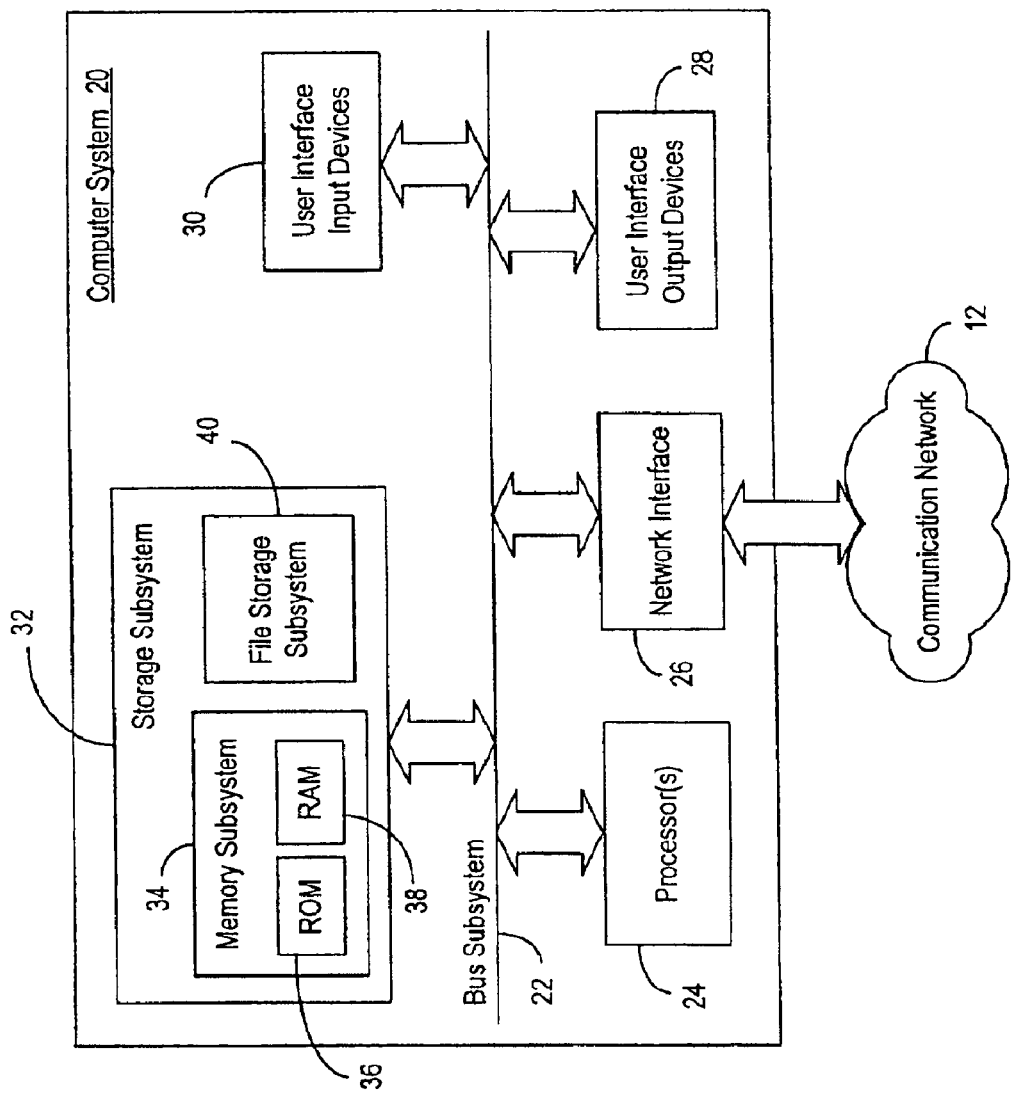
FIG. 2 is a simplified block diagram of a computer system according to an embodiment of the present invention.

FIG. 2 is a simplified block diagram of computer system 20 according to an embodiment of the present invention. Computer system 20 typically includes at least one processor 24, which communicates with a number of peripheral devices via bus subsystem 22. These peripheral devices typically include a storage subsystem 32, comprising a memory subsystem 34 and a file storage subsystem 40, user interface input devices 30, user interface output devices 28, and a network interface subsystem 26. The input and output devices allow user interaction with computer system 20. It should be apparent that the user may be a human user, a device, another computer, and the like. Network interface subsystem 26 provides an interface to outside networks, including an interface to communication network 12, and is coupled via communication network 12 to corresponding interface devices in other computer systems.

User interface input devices 30 may include a keyboard, pointing devices such as a mouse, trackball, touchpad, or graphics tablet, a scanner, a touchscreen incorporated into the display, audio input devices such as voice recognition systems, microphones, and other types of input devices. In general, use of the term "input device" is intended to include all possible types of devices and ways to input information into computer system 20 or onto computer network 12.

User interface output devices 28 may include a display subsystem, a printer, a fax machine, or non-visual displays such as audio output devices. The display subsystem may be a cathode ray tube (CRT), a flat-panel device such as a liquid crystal display (LCD), or a projection device. The display subsystem may also provide non-visual display such as via audio output devices. In general, use of the term "output device" is intended to include all possible types of devices and ways to output information from computer system 20 to a human or to another machine or computer system.

Storage subsystem 32 stores the basic programming and data constructs that provide the functionality of the various systems embodying the present invention. For example, the various modules implementing the functionality of the present invention may be stored in storage subsystem 32. These software modules are generally executed by processor 24. In a distributed environment, the software modules may be stored on a plurality of computer systems and executed by processors of the plurality of computer systems. Storage subsystem 32 also provides a repository for storing the various databases storing information according to the present invention. Storage subsystem 32 typically comprises memory subsystem 34 and file storage subsystem 40.

Memory subsystem 34 typically includes a number of memories including a main random access memory (RAM) 38 for storage of instructions and data during program execution and a read only memory (ROM) 36 in which fixed instructions are stored. File storage subsystem 40 provides persistent (non-volatile) storage for program and data files, and may include a hard disk drive, a floppy disk drive along with associated removable media, a Compact Digital Read Only Memory (CD-ROM) drive, an optical drive, removable media cartridges, and other like storage media. One or more of the drives may be located at remote locations on other connected computers at another site on communication network 12. Information stored according to the teachings of the present invention may also be stored by file storage subsystem 40.

Bus subsystem 22 provides a mechanism for letting the various components and subsystems of computer system 20 communicate with each other. The various subsystems and components of computer system 20 need not be at the same physical location but may be distributed at various locations within distributed network 10. Although bus subsystem 22 is shown schematically as a single bus, alternate embodiments of the bus subsystem may utilize multiple busses.

Computer system 20 itself can be of varying types including a personal computer, a portable computer, a workstation, a computer terminal, a network computer, a television, a mainframe, or any other data processing system. Due to the ever-changing nature of computers and networks, the description of computer system 20 depicted in FIG. 2 is intended only as one example, only for purposes of illustrating an embodiment of the present invention. Many other configurations of a computer system having more or less components than the computer system depicted in FIG. 2 also find use. Client computer systems 16 and server computer systems 14 may have the same configuration as shown in FIG. 2, with the server systems generally having more storage capacity and computing power than the client systems.

2) Workflow

Figure 3:
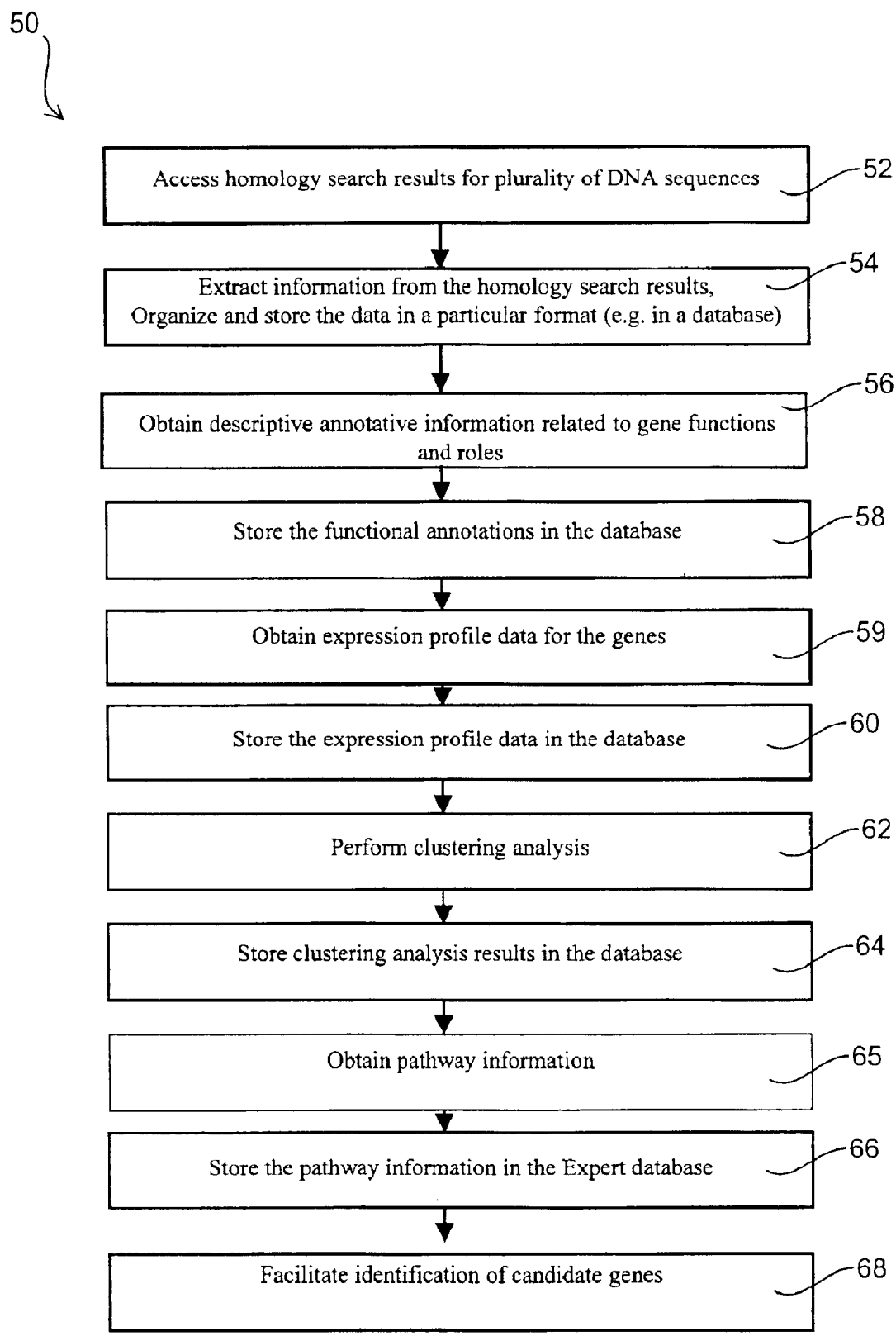
FIG. 3 is a simplified flowchart showing processing performed by an embodiment of the present invention to facilitate identification of candidate genes from a plurality of input DNA sequences.

FIG. 3. depicts a simplified flowchart showing processing performed by an embodiment of the present invention to facilitate identification of candidate genes from a plurality of input DNA sequences. As shown in FIG. 2, processing is initiated when the server system 14 accesses results of a homology search from the plurality of input DNA sequences 52. These steps are typically performed by client, or server, or by a plurality of servers.

The present invention then extracts relevant information from the homology analysis output as described above for each input DNA sequence, organizes the information, and stores it in a format which facilitates further processing and analysis of the information 54. Typically at least the name of the gene represented by a nucleotide sequence is stored in a database, however more functional annotative information may be stored for the genes according to an embodiment of the present invention, for example, the sequence name, best BLAST hits, and its biological role or multiple roles deduced from the best BLAST or Smith-Waterman hits.

Server 14 then obtains descriptive annotative information on the biochemical function(s) and the physiological role(s) for the known genes from the plurality of nucleotide sequences 56 and stores the information in an expert database 58. Several different techniques may be used by the present invention to obtain the functional information, including information extraction.

The present invention then obtains 59 and stores 60 expression profile data for the genes and their homologs. Profiles can be created for genes expressed in cells or tissues under influences of an agent, as a cell or tissue develops, or during changes to the physiological state of the cell or tissue, or in response to the development of disease in humans or an animal model. The corresponding nucleotide sequences may then be clustered by their expression patterns by one of any number of means 62 and the clustering analysis is stored in a database 64.

In one embodiment of the present invention, pathway information, represented as cross-referenced information about the biological relationships of genes represented by the nucleotide sequences and their homologs, is obtained 65 from literature databases such as MEDLINE by natural language processing and information extraction procedures, cross-referenced, and may be stored 66 in the expert database for convenient viewing by a user. Other public literature databases include, without limitation, the Kyoto Encyclopedia of Genes and Genomes (KEGG) or the Munich Information Center for Protein Sequences (MIPS), the U.S.P.T.O. and W.I.P.O. patent database, the Online Mendelian Inheritance in Man (OMIM) database etc. Additional annotative information concerning, for example, genes and diseases or gene expression information may be obtained and processed from the above databases.

The information stored in the databases according to the present invention facilitates the identification of candidate genes 68. In particular, the combination of gene expression profile data and pathway information generated through computer implemented natural language processing and information extraction facilitates the identification of candidate genes. A more detailed description of the methods is given below.

3) Homology Search Results

The nucleotide sequences which are input as queries to the homology search are generally obtained from complementary cDNA sequences which have been synthesized using isolated messenger RNA (mRNA; the transcription products of expressed genes). The cDNA sequences are used as input sequences to the homology search analysis since cDNAs represent expressed genomic regions and are thus believed to identify parts of the genome with the most biological and medical significance.

As part of the homology search, nucleotide and protein sequence databases are searched to find sequences that are related to the input or query nucleotide sequences. For example, given a set of differentially expressed query sequences, corresponding to the mRNA of their cognate genes, a homology search identifies known, similar and unknown genes. A homology search is generally performed by using computer-implemented search algorithms to compare the query sequence with sequence information stored in a plurality of databases accessible via a communication network, for example, the Internet. Examples of such algorithms include the Basic Local Alignment Search Tool (BLAST) algorithm, the PSI-blast algorithm, the Smith-Waterman algorithm, the Hidden Markov Model (HMM) algorithm, and other like algorithms. For example, a "blastn" program utilizing the BLAST algorithm may be used to search the Genbank database for homologs of the query cDNA sequences. According to an embodiment of the homology search, the query cDNA sequences may be grouped as "known," "unknown," or "similar" sequences. "Known" cDNA sequences include sequences with substantial sequence identity to existing sequence entries in a sequence database, such as the GenBank database. "Unknown" cDNA sequences include sequences similar to existing sequence entries in a sequence database but lacking functional annotation, or those sequences with no matching sequences in existing sequence databases. "Similar" cDNA sequences include sequences for which no matches are found in the sequence database, but which exhibit similarity, as defined below, to existing entries in sequence databases.

Two or more sequences, either polynucleotide or polypeptide, may exhibit "substantial sequence identity" if the sequences have at least 70%, preferably 80%, most preferably 90%, 95%, 98% or 99% nucleotide or amino acid residue identity, when compared and aligned for maximum correspondence, as measured using a particular sequence comparison algorithm or by using visual inspection.

Several different sequence comparison algorithms may be used. According to a first technique, using global or local alignments, two sequences (amino acid or nucleotide) can be compared over their full-length (e.g. the length of the shorter of the two, if they are of substantially different lengths) or over sub-sequences of 200, at least about 200, at least about 500 or at least about 1000 contiguous nucleotides or at least about 40, at least about 50, or at least about 100 contiguous amino acid residues. According to an embodiment of the present invention, a query sequence may qualify as a "known" gene if the query DNA sequence meets the following stringent criteria: (1) a sequence length greater than 200 nucleotides with greater than or equal to 80% identity over 70% of the query sequence length with an E-value (a probability value of a match occurring if the sequence were randomized) of less than $1^{e-50}$; and (2) for the predicted amino acid homology, greater than or equal to 80% identity for a segment length greater than 50 amino acids and an E-value of less than $1^{e-20}$. Sequences that meet either, but not both, the nucleotide or polypeptide sequence criteria may be grouped as "similar" genes after examination of the respective nucleic acid or amino acid alignments.

For sequence comparison, typically one sequence acts as a reference sequence, to which test sequences are compared. When using a sequence comparison algorithm, test and reference sequences are input to a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

As stated above, a plurality of homology search algorithms may be used to determine optimal alignment of sequences. These include the local homology algorithm of Smith & Waterman, Adv. Appl. Math. 2:482 (1981), the homology alignment algorithm of Needleman & Wunsch, J. Mol. Biol., 48:443 (1970), the similarity method of Pearson & Lipman, Proc. Natl. Acad. Sci. USA 85:2444 (1988), the PSI-Blast homology algorithm of Altschul et al., Nucleic Acids Res. 25:3389–402 (1997), the computerized implementations of algorithms GAP, BESTFIT, FASTA, and TFASTA included in the Wisconsin Genetics Software Package, Genetics Computer Group, 575 Science Dr., Madison, Wis.), by Hidden Markov Models (HMM, Durbin, Eddy, Krogh & Mitchison, Cambridge University Press, 1998), or EMotif/EMatrix to identify sequence motifs (Nevill-Manning, Wu, & Brutlag, Proc Natl. Acad. Sci U S A. 1998 May 26;95(11):5865–71), or by visual inspection (see generally Ausubel et al., supra). Each of the above identified algorithms and the references are herein incorporated by reference in its entirety for all purposes. These algorithms are well known to one of ordinary skill in the art of molecular biology and bioinformatics. When using any of the aforementioned algorithms, the default parameters for "Window", gap penalty, etc., are usually used. Practitioners of the art molecular biology with average skill will recognize these parameters as: (a) the "window" is typically a 9, 10 or 11 nucleotide word length of sequence over which the homology is determined; and (b) gap penalty is a scoring value to prevent large gaps from occurring in reported alignments.

The BLAST algorithm is welt suited for determining percent sequence identity and sequence similarity. The BLAST algorithm is described in Altschul et al., J Mol. 215:403–410, (1990), the entire contents of which are herein incorporated by reference for all purposes. Several software programs incorporating the BLAST algorithm are publicly available through the National Center for Biotechnology Information (NCBI). These programs include the blastp, blastn, blastx, tblastn, tblastx, and PSI-blast software programs. Due to codon wobble or species differences, more informative homologies can be found by comparing the predicted protein sequence of a DNA query sequence to a protein sequence database. For this task, the Smith-Waterman or PSI-BLAST algorithms may be used. Similarly, for weak homologs, functional domains of proteins may be discerned by Smith-Waterman, HMM or Emotif algorithms. Software for performing HMM and Smith-Waterman analysis can be obtained from a variety of public sources and/or from vendors that sell accelerated computer hardware to rapidly process large batches of sequences (e.g. Paracel, Pasadena, Calif. TimeLogic, Crystal Bay, Nev.). Software for EMotif/Ematrix can be obtained from sources such as the Brutlag Bioinformatics Group, Stanford University, Stanford, Calif.

The BLAST heuristic search algorithm is optimized for speed and searches sequence databases accessible to server 14 for optimal local alignments to the input query nucleotide sequences. Databases which may be searched using the BLAST programs include the SWISS-PROT protein sequence database, GenBank database, the Genome Sequence database (GSDB), the European Molecular Biology Laboratory (EMBL) Nucleotide Sequence database, the DNA Database of Japan (DDBJ), and other like databases.

The BLAST algorithm identifies high scoring sequence pairs (HSPs) by identifying short words of length "W" in the query cDNA sequence, which either match or satisfy some positive-value threshold score "T" when aligned with a word of the same length in a database sequence. "T" is referred to as the neighborhood word score threshold (Altschul et al, supra). An "X" parameter is a positive integer representing the maximum permissible decay of the cumulative segment score during word hit extension. These initial neighborhood word hits act as seeds for initiating searches to find longer HSPs containing them. The word hits are then extended in both directions along each sequence for as far as the cumulative alignment score can be increased. Extension of the word hits in each direction are halted when the cumulative alignment score goes to zero or below, due to the accumulation of one or more negative-scoring residue alignments, or when the end of either sequence is reached. The BLAST algorithm parameters "W", "T", and "X" determine the sensitivity and speed of the alignment. Accordingly, the stringency of a BLAST search can be adjusted by appropriately setting the search parameters. However, if the search parameters are too loose, an excessive amount of biologically questionable "hits" may be returned. The BLAST program uses as defaults a wordlength (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=4, and a comparison of both strands. Typically, the default parameters can yield from zero to scores of likely homologs for the input query DNA sequences.

In addition to calculating percent sequence identity, the BLAST algorithm also performs a statistical analysis of the similarity between two sequences (see, e.g. Karlin & Altschul, Proc. Natl. Acad. Sci. USA 90:5873–5787 (1993)). One measure of similarity provided by the BLAST algorithm is the smallest sum probability (P(N) or E-value as an expected value), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about 0.001, and most preferably less than about 0.0001.

A further indication that two nucleic acid sequences or polypeptides are substantially identical is that the polypeptide encoded by the first nucleic acid is immunologically cross reactive with the polypeptide encoded by the second nucleic acid. Thus, a polypeptide is typically substantially identical to a second polypeptide, for example, where the two peptides differ only by conservative substitutions.

As is well known to one of ordinary skill in the art, results from a homology search or analysis include: a plurality of query sequences; a list of homologous (target) sequences; an E-Value that describes the probability that the original (query) sequence match with the target sequence could occur randomly; the annotation of the target sequence, if provided; an alignment of the query sequence to each target sequence; the percent identity of the query sequence to the target sequence; the hit length, or length of the sequence over which the percent identity is determined.

Figure 4:
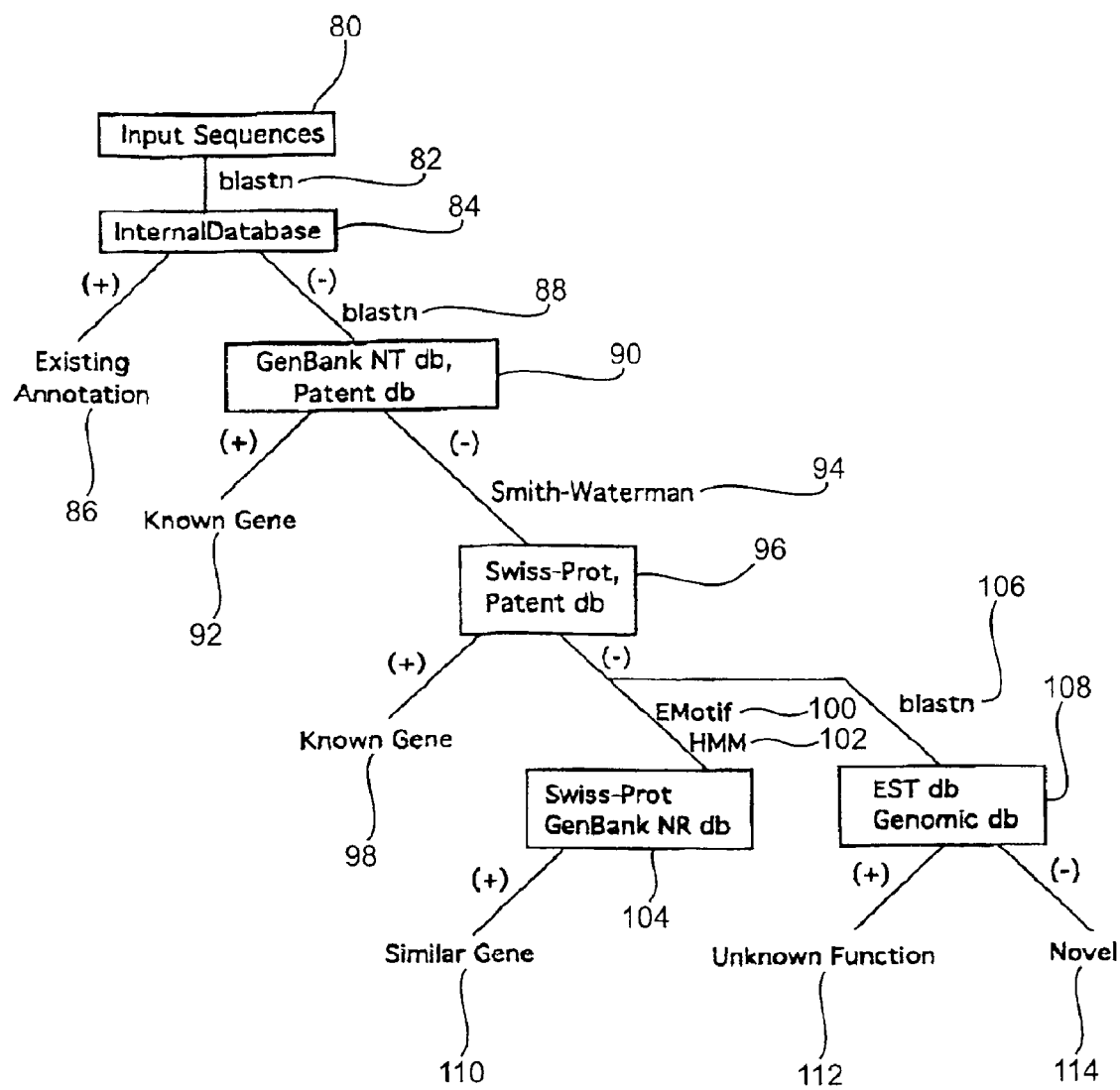
FIG. 4 depicts a process of performing homology analysis for a plurality of sequences according to an embodiment of the present invention.

The complete homology analysis of a plurality of sequences according to an embodiment of the present invention is composed of a process described in FIG. 4. The output(s) from the process shown in FIG. 4 may be used as the input to step 52 in FIG. 3. The rationale for this sequential strategy of homology analysis is to automate the method of sequence classification. According to the embodiment shown in FIG. 4, input sequences 80 are subjected to BLAST analysis 82 against an internal database of sequences 84. Near identical homologs (E-value<$1^{e-80}$) are sieved and recorded as being strong homologs of previously classified entries 86 of the internal database. Those sequences failing this test, are subjected to blastn analysis 88 against the GenBank nucleotide (NT) and patent databases 90. Those sequences showing strong similarity (E-value <$1^{e-50}$ with sequence length>200 nucleotides, 80% identity over 70% of the query sequence length) are classified as "known" genes 92. Those sequences failing this test are subjected to Smith-Waterman analysis 94 against the protein databases of Swiss-Prot and the translated patent database 96. Those sequences with E-values<$1^{e-20}$ with 80% identity over a segment length>50 amino acids are classified as "known" genes 98 while sequences with an E-value >$1^{e-20}$ are subjected in parallel to (a) HMM 102 and EMotif 100 analysis against the Swiss-Prot and GenBank non-redundant (NR) protein databases 104 and (b) BLASTN analysis 106 against the GenBank EST and genomic databases 108. Those sequences with an E-value<$1^{e-9}$ after HMM or EMotif are scored as "Similar" genes 110 while sequences with an E-value<$1^{e-60}$ after the final BLASTN analysis 106 are classified as "unknown" 112. Any sequences failing this last test are classified as "Novel" 114.

Figure 7:
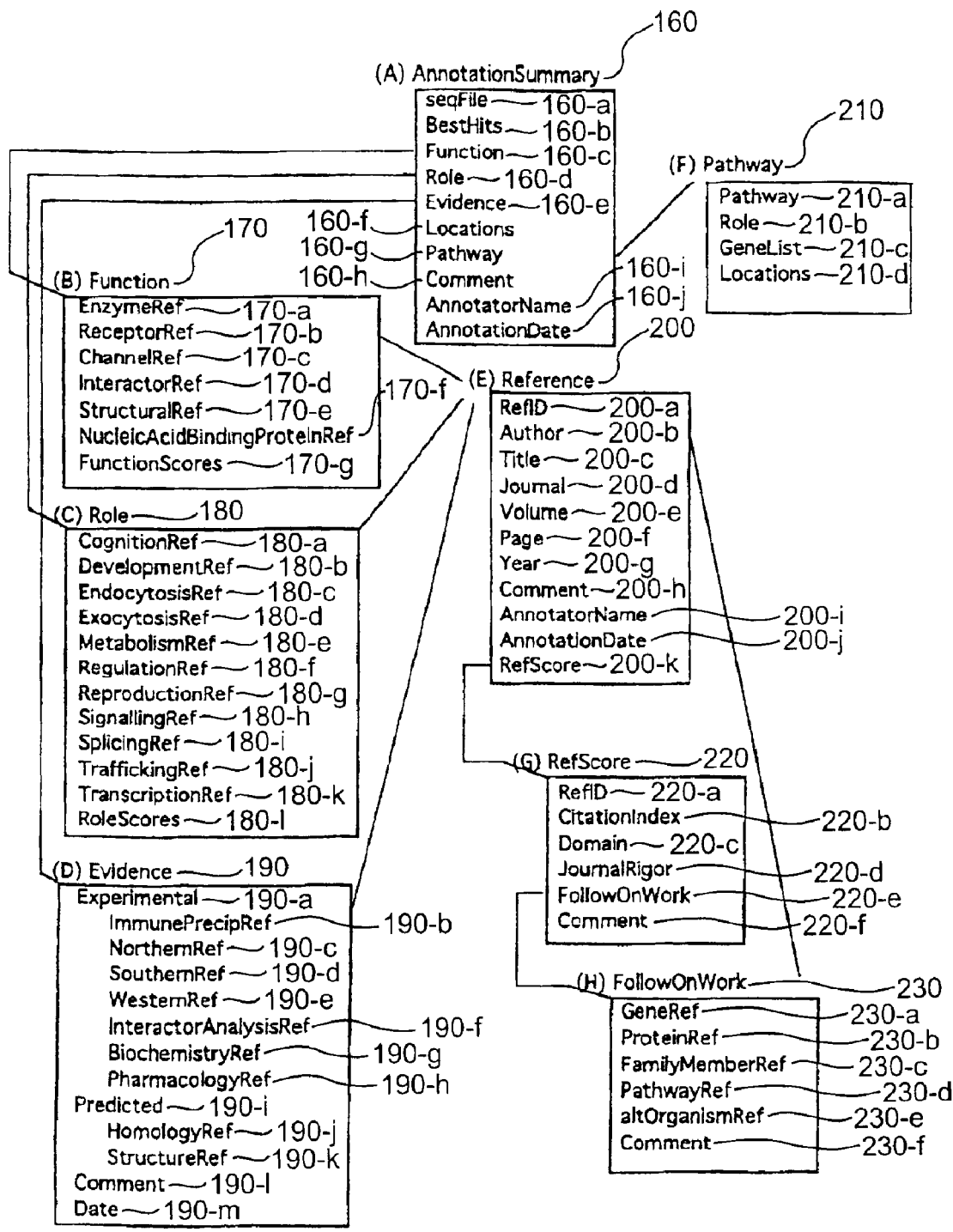
FIG. 7 depicts a database schema showing the functional annotative information stored for the genes according to an embodiment of the present invention. This database is the expert database.
Figure 8:
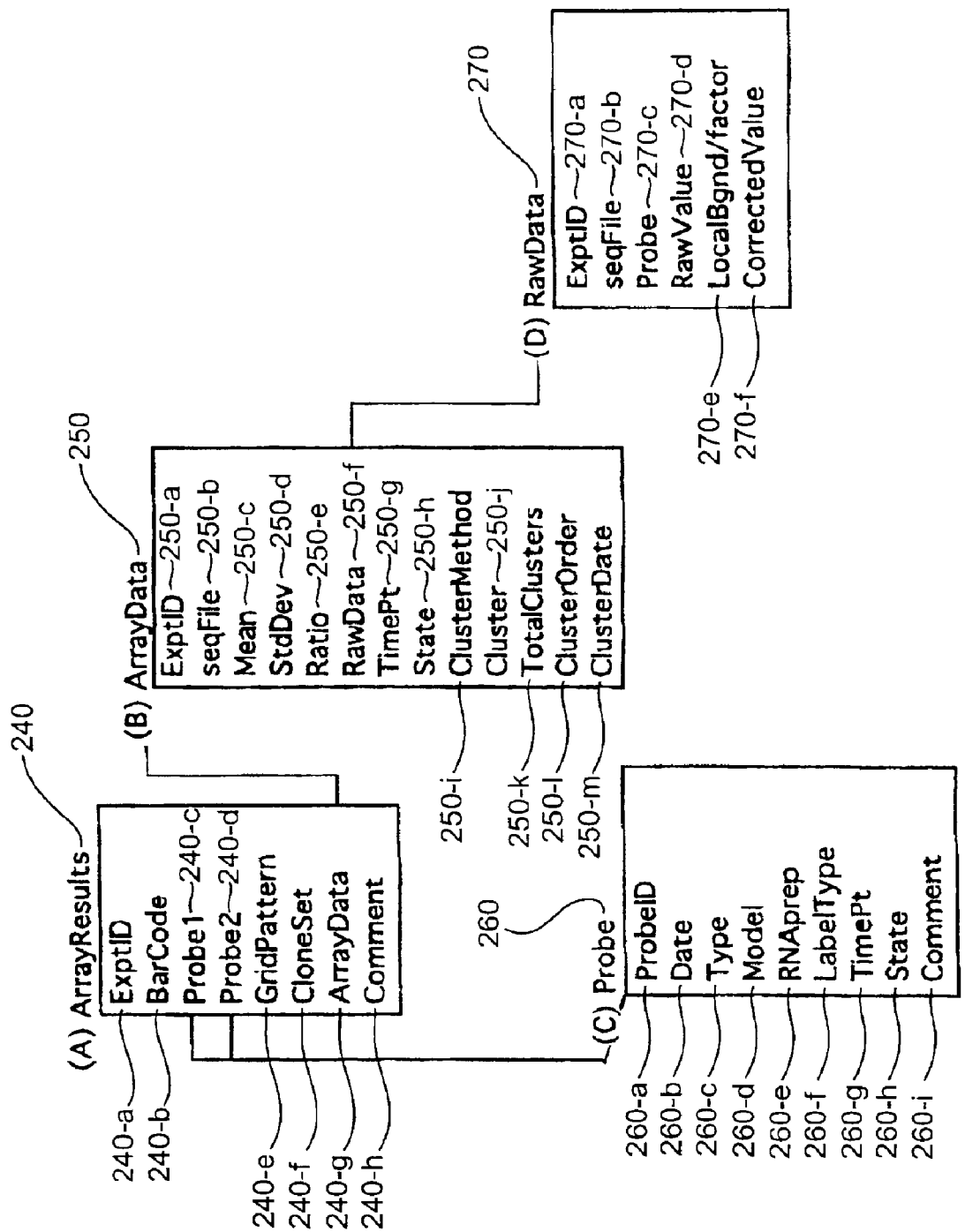
FIG. 8 depicts a database schema showing the gene expression profile data stored for the genes according to an embodiment of the present invention. This database is the gene expression database.

Methods of the present invention extract relevant information from the homology analysis output as described above for each input DNA sequence, organize the information, and store it in a format which facilitates further processing and analysis of the information (step 54). According to an embodiment of the present invention, the information extracted from the BLAST, Smith-Waterman and HMM search output is stored in a database. The information extracted and stored by the present invention during step 54 is shown by the database schema depicted in FIG. 5. FIGS. 7 and 8 depict other database structures for storing information according to an embodiment of the present invention.

Figure 5:
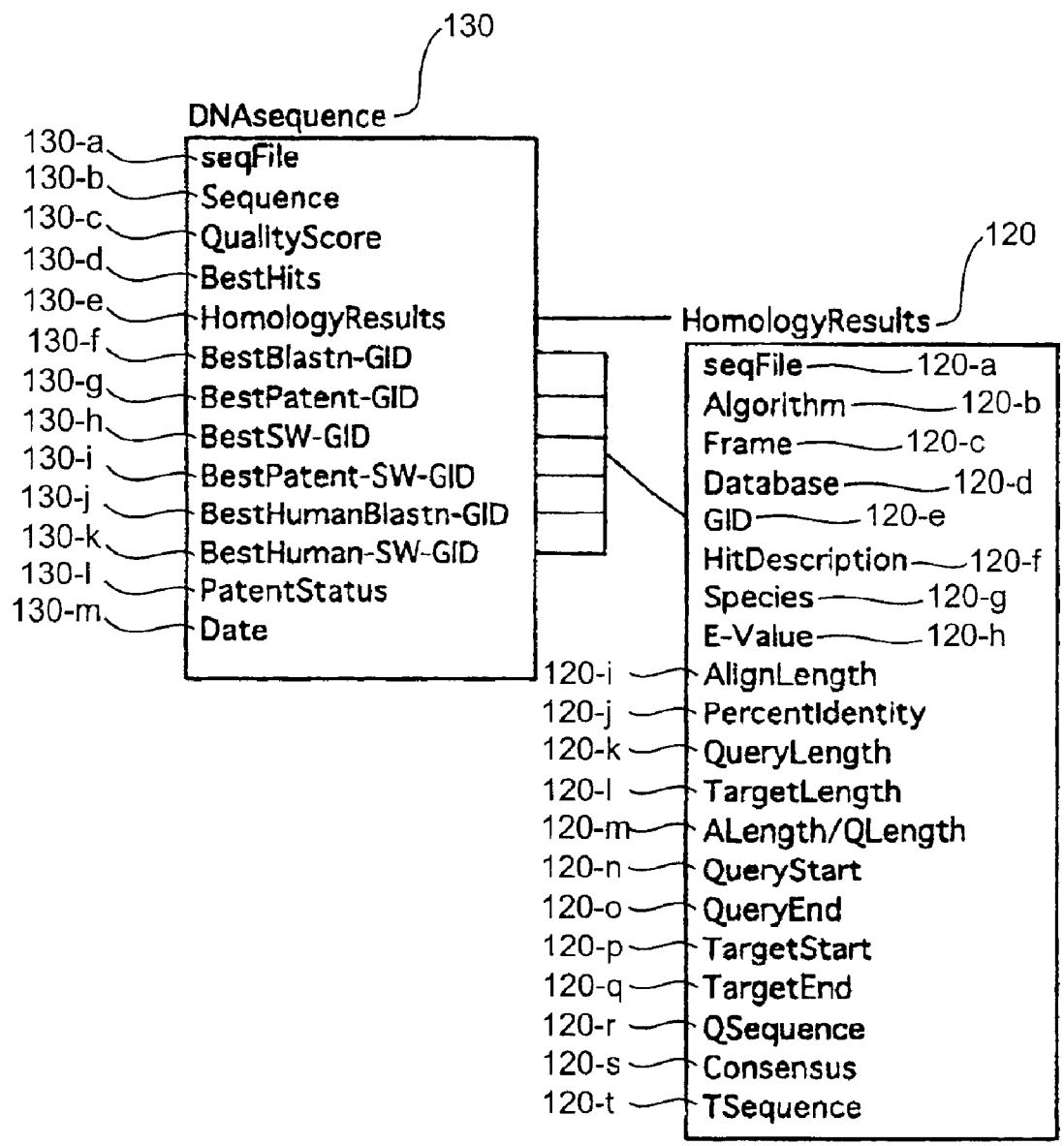
FIG. 5 depicts a database schema showing information extracted from homology search results and stored for the DNA sequences according to an embodiment of the present invention. This database is the DNA sequence database.

FIG. 5 shows information (database table "HomologyResults" 120) which is extracted from the homology search results, and stored for each query cDNA sequence according to an embodiment of the present invention. It is important to note that multiple (typically 10) homologs for each query sequence are stored in this database table in order to facilitate extraction of the most descriptive and accurate annotation for the query sequence. It should also be evident that various other formats, in addition to tables and databases, may also be used to store the information. The following scenario is common: the top 1, 2, 3, 4 or 5 blastn homologs of a query have E-values within a 10-fold range and are<$1^{e-50}$ yet lack informative annotative information (e.g. such homologs are expressed sequence tags or genomic DNA). However, the second, third, fourth, fifth, sixth or seventh homolog's E-values might have the following attributes: the E-value is less than $1^{e-50}$ and is within 10 or 100 fold of the top hit but the weaker homolog's annotation might provide more informative description of the query sequence's role or function; e.g. the weaker homolog might be an enzyme, receptor or structural protein. Identification of these more accurate descriptions is facilitated by a combination of keyword tables and information extraction methods described herein. In these circumstances, those of normal skill in the art of bioinformatics will recognize that the weaker hit provides the most useful annotation, provided that the E-value meets the above criteria.

For each homolog, the present invention stores, in database tables "DNAsequence" 130 and "HomologyResults" 120, the name of the sequence (attribute "seqFile" 130-a and 120-a), the sequence ("Sequence" 130-b), the quality scores or Phred values (Ewing, Hiller, Wendl & Green, Genome Research, 8:175–185, 1998), ("QualityScores" 130-c), the accession number of any homolog, i.e. the GenBank identifier number ("GID" 120-e), the best GID derived from BLAST analysis ("BestBlastnGID" 130-f), the best GID derived from BLAST against the patent DNA database analysis ("BestPatent-GID" 130-g), the best GID derived from Smith-Waterman analysis derived from the Swiss-Prot database ("BestSW-GID" 130-h), the best GID derived from Smith-Waterman analysis of the patent (database "BestPatent-SW-GID" 130-i), the best GID derived from the best human homolog in BLAST analysis ("BestHumanBlastn-GID" 130-j), and the best GID derived from the best human homolog derived from Smith-Waterman analysis ("BestHuman-SW-GID" 130-k). For any homolog, the algorithm (e.g. BLAST or HMM) used for the homology search is recorded ("Algorithm" 120-b), the frame of the predicted protein for protein comparisons ("Frame" 120-c), the database searched ("Database" 120-d), the GenBank annotation for any homolog ("HitDescription" 120-f), the species of the annotation ("Species" 120-g), the E-value ("E-value" 120-h), the length of the alignment region ("AlignLength" 120-i), the percent identity of the aligned sequences ("PercentIdentity" 120-j), the length of the query in the alignment ("QueryLength" 120-k), the length of the target in the alignment ("TargetLength" 120-l), a number representing the fraction of the total query length represented in the hit region ("ALength/QLength" 120-m), the start position of the query sequence in the alignment ("QueryStart" 120-n), the position of the end of the query ("QueryEnd" 120-o), the start position of the target sequence ("TargetStart" 120-p), the end position of the target sequence ("TargetEnd" 120-q), the query sequence in the alignment ("QSequence" 120-r), the consensus of the alignment ("Consensus" FIG. 120-s), and the target sequence in the alignment ("TSequence" 120-t).

4) Annotation of DNA Sequences with Functional Information

Figure 6:
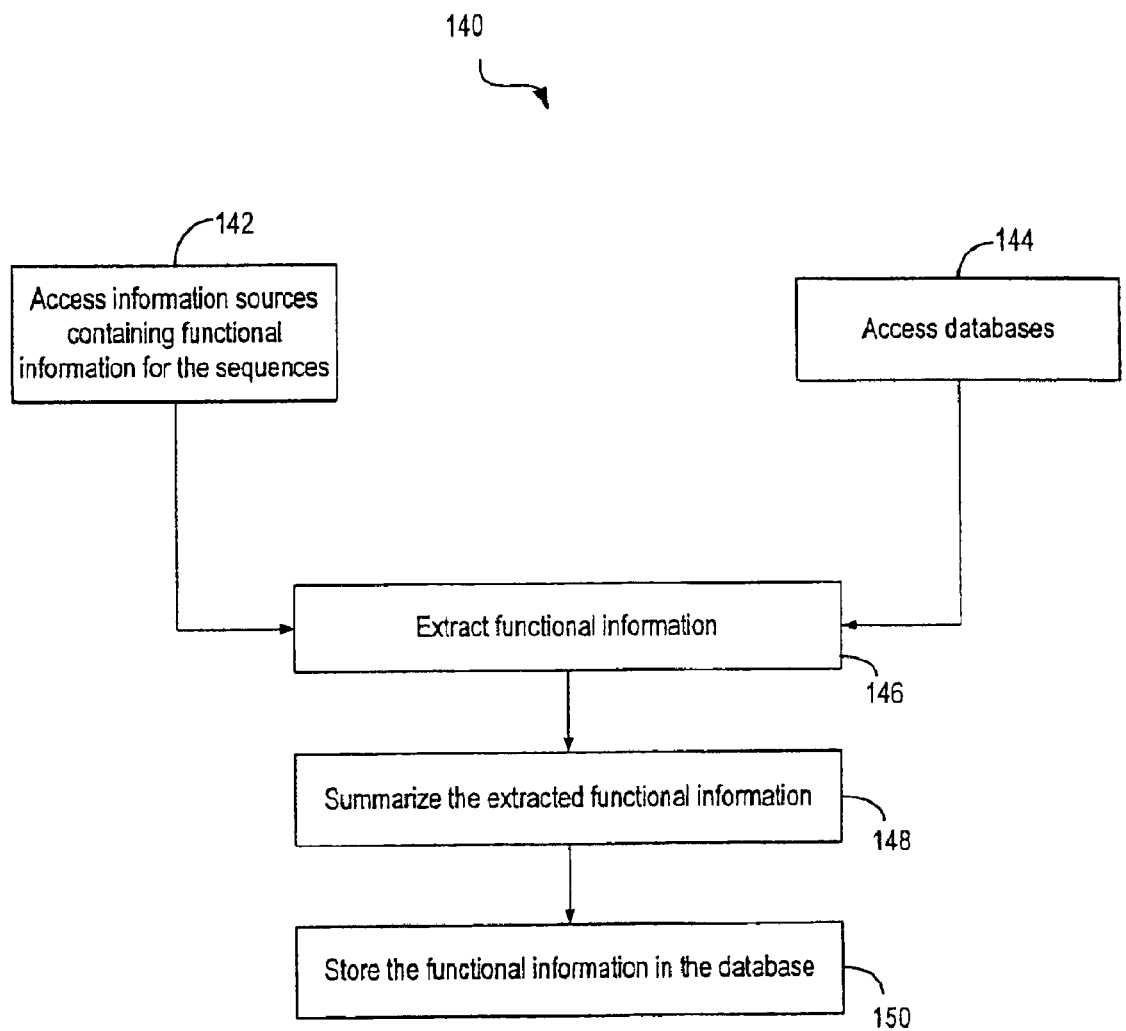
FIG. 6 is a simplified flowchart showing processing performed by an embodiment of the present invention for obtaining descriptive annotative information for the genes.

Referring back to FIG. 3, server 14 then obtains (step 56) descriptive annotative information on the biochemical function(s) and the physiological role(s) for the known genes from the plurality of cDNA sequences and stores the information in the database (step 58). FIG. 6 depicts a simplified flowchart 140 showing processing performed by an embodiment of the present invention for obtaining descriptive annotative information for the known genes. As shown in FIG. 6, several different techniques may be used by the present invention to obtain the functional information. According to a first technique, the present invention accesses information sources containing functional information related to the known genes (step 142). The information sources may include articles, published material, and other like material accessible to server 14. According to a specific embodiment, the present invention may use the accession numbers or the GenBank identifiers (GIDs) associated with the DNA sequences and their homologs to find the published material. Text processing tools may then be used by the present invention to automatically extract functional information from the information sources accessed in step 142 (step 146). The extracted information may then be summarized (step 148) and stored in the database (step 150).

According to another technique, the present invention may obtain the functional information from databases storing functional information and which are accessible to server 14 (step 144). Examples of such databases include databases provided by Proteome of Boston, Mass., DoubleTwist of Oakland, Calif., of Rockville, Md., the Genbank database of deposited DNA and protein sequence data, the SWISS-PROT protein database, the PubMed or Medline (NCBI) databases of abstracts derived from thousands of peer-reviewed biomedical journals, and other like databases. The Proteome databases are concise descriptions of known genes, their protein products and their functions and roles and known interactors as described in the current literature. The information extracted from the published material and genomic databases may then be summarized (step 148) and stored in the database (step 150).

The GenBank record of a cDNA or gene sequence commonly contains references to peer-reviewed publication information, stored in the Medline database about the gene. The Medline database can be accessed via the Internet via the PubMed interface. Alternatively, the GenBank record contains informative keywords related to the gene which may be used to perform broad topic searches on the Medline database. For example, protein products of genes participate in many processes essential to metabolism, development and reproduction. In some cases, a protein encoded by a gene may have more than one function and/or more than one role. For example, the yeast inositol 1-4-5 triphosphate kinase enzyme adds a phosphate moiety to phosphoinositol—an important component involved in signaling. However, this protein also can act as a regulatory scaffolding protein for transcription factors in the nucleus (Audrey R. et al. Science 287:2026–2029, 2000). Thus, this single protein can function as both an enzyme and a structural protein. Similarly, this gene product has two roles: it can participate in signaling processes and mRNA transcription. These instances are also examples of general pathways but further annotative information from the published literature may refine these topics to even more specific pathways. For example, the enzymatic activity might be most important for a growth hormone pathway and the structural role might be more important to a specific subset of transcription factors engaged in controlling cell division. In this invention, these relational links between genes and cellular or organismal processes constitute a web of interacting pathways that are extracted accurately and comprehensively.

There is a demand for biological information extraction from published material, such as abstracts, etc., in a comprehensive and consistent manner. Traditionally, extraction of information has been done manually with varying degrees of consistency and accuracy. With recent advances in information extraction technologies, various software programs have been developed to automate information extraction and to summarize the extracted information. Examples of such programs include programs provided by InXight Corp. of Santa Clara, Calif. Another example of a software package for information or knowledge extraction is the Crystal-Badger-Marmot suite from the Center for Intelligent Information Retrieval, Univ. of Massachusetts, Amherst, Mass. Such software programs have been applied to extract information from abstracts of published papers as well as from full-text papers. According to an embodiment of the present invention, these techniques are applied to generate tables of genes, tables of pathways composed of genes, and tables of relationships between and amongst genes and pathways. As described below, the relationship between or amongst genes is validated in a quantitative fashion.

According to an embodiment of the present invention, information extraction programs, such as those discussed above and others, are used to extract (step 146 in FIG. 6) descriptive annotation information from information accessible to server 14 and to summarize (step 148 in FIG. 6) the information. According to an aspect of the present invention, the annotative information is stored in a database.

According to the present invention, information may be extracted and stored for both the majority views and potentially multiple minority views. This is due to dramatic shifts in the understanding of biological systems over time. These shifts are also referred to as "paradigm shifts" (Kuhn, T., The Structure of Scientific Revolutions, Univ. Chicago Press 1962). According to these paradigm shifts, a minority view becomes accepted as being the correct interpretation after critical new data is acquired. The change in accepted "truth" of a paradigm can be dramatic or subtle in various domains of knowledge, and in the realm of biology both extremes can occur—hence the need for comprehensive collections of entity-relationships amongst genes, functions, roles and pathways. The need for dynamically storing both the majority and minority views becomes important when one realizes that much remains to be known about the laws of biology. This is substantially different from other techniques which only store information related to the majority view (e.g. T. Rindflesch, L. Tanabe, J. Weinstein & L. Hunter PSB 2000:517–528).

For example, for a given biological topic, perhaps about 51, about 75, or about 90 out of 100 published abstracts may describe a phenomenon as being caused by the interactions of genes A and B whereas a smaller subset of abstracts, perhaps about 10, about 25 or about 49 describe a more complex interaction between genes A and C prior to gene B. The former A-B model would be considered the consensus, "majority view" model (a "truth") and the latter A-C-B model would be considered a "minority view" and likely regarded as being "false." According to traditional bioinformatics techniques, only information related to strict "truths" was maintained and information related to the minority view(s) was discarded to reduce the amount of data being stored.

According to an embodiment of the present invention, minority views (e.g. unusual or unexpected relationships between genes or metabolic pathways) are also stored in the database but assigned a lower reference score (see "RefScore "attribute 200-*k* in table "Reference" 200 in FIG. 7, "FunctionScores" attribute 170-*g* in table "Function" 170, "RoleScores" attribute 180-*l* in table "Role" 180, and attributes 220-*a* through 220-*f* of table "RefScore" 220) associated with the descriptive annotation of the known genes from the plurality of cDNA. The reference score (or their summary scores, "FunctionScores" 170-*g* and "RoleScores" 180-*l*) quantifies the "acceptance/majority opinion" for an alleged role or function of a gene. Of particular importance to "minority" views is the extraction and recording of special circumstances or boundary conditions under which the phenomena or relationship amongst genes might exist.

The metric for evaluating a specific published reference article also assigns a score derived from the Citation Index database (Institute for Science Information, Philadelphia) which quantitatively ranks the impact of a given paper by the number of times that paper is subsequently referenced. For the most significant papers, a published article can be referenced thousands of times. The Citation Index also ranks journals with high impact but only from the same criteria of frequently-cited papers from the journals regardless of whether the published paper is ultimately revised or shown to be inaccurate or limited to a set of conditions. Hence, one embodiment of this invention provides a mechanism to take into account the quality of the information source. This is both general and a specific measure. In general, articles in journals respected by a consensus of biomedical and genomics practitioners are believed to be reliable. For example, a publication in journals with a recognized, rigorous peer-review process (e.g. Science, Nature, the Journal of Biological Chemistry, or the Journal of Clinical Investigations) would receive 100 points or>90 points whereas publication in "lesser" journals (e.g. Journal of Antisense Research or Experimental Cell Research) would only receive 10 or 40 points.

Table 1 is an exemplary look-up table for general rankings of such biomedical journals. However, scores from table 1 may be adjusted because the information source's peer-review process can be dependent upon the reviewers for a given domain or the degree of democratic consensus of a journal's editorial board. A domain specific weighting factor is derived for the major journals and can be applied systematically while in other cases, a human annotator must make the judgment. The adjustment can range between 10 and 50% of the original score and an article in a "lower-quality" journal can be upgraded or an article in a "higher-quality" journal can be downgraded.

TABLE 1

| Score | Journal |
|-------|---------|
| 100 | Nature |
| 100 | Science |
| 97 | Cell |
| 96 | Neuron |
| 96 | Nature Structural Biology |
| 95 | Nature Cell Biology |
| 95 | Nature Genetics |
| 95 | Nature Medicine |
| 95 | Nature Neuroscience |
| 94 | Journal of Structural Biology |
| 94 | New England Journal of Medicine |
| 92 | Journal of Biological Chemistry |
| 92 | Journal of Molecular Biology |
| 92 | Neuroscience |
| 91 | Journal of Bacteriology |
| 91 | Journal of Cell Biology |
| 91 | Journal of Immunology |
| 91 | Journal of Neurochemistry |
| 90 | Biochemistry |
| 90 | Bioinformatics |
| 90 | Immunology |
| 90 | Journal of Clinical Investigation |
| 90 | Journal of Internal Medicine |
| 90 | Journal of Medicinal Chemistry |
| 90 | Journal of Membrane Biology |
| 90 | Journal of Neuroscience |
| 90 | Journal of Virology |
| 90 | Molecular Microbiology |
| 89 | Cell Biology |

TABLE 1-continued

| Score | Journal |
|---|---|
| 89 | Genetics |
| 89 | Journal of Experimental Medicine |
| 89 | Journal of Neurobiology |
| 89 | Neurology |
| 88 | Infection and Immunity |
| 87 | Journal of Neuroendocrinology |
| 87 | Journal of Neuroimmunology |
| 87 | Journal of Neurology |
| 87 | Neuroendocrinology |
| 86 | Neuroscience Letters |
| 85 | Development |
| 85 | Proceedings National Academy of Sciences |
| 85 | Immunogenetics |
| 85 | Journal of Cell Science |
| 85 | Journal of Infectious Diseases |
| 85 | Journal of Neurophysiology |
| 85 | Molecular Pharmacology |
| 85 | Molecular and Cellular Biology |
| 84 | Brain Research |
| 84 | Developmental Biology |
| 84 | Developmental Neuroscience |
| 84 | Molecular Biology of the Cell |
| 83 | Cancer |
| 82 | Analytical Biochemistry |
| 82 | Journal of Endocrinology |
| 82 | Journal of Experimental Biology |
| 82 | Journal of Histochemistry and Cytochemistry |
| 82 | Journal of Molecular Endocrinology |
| 82 | Molecular Immunology |
| 82 | Natural Immunity |
| 82 | Nucleic Acids Research |
| 80 | Brain |
| 80 | Journal of Physiology |
| 80 | Molecular and Cellular Endocrinology |
| 80 | Molecular and Cellular Neurosciences |
| 78 | Genome Research |
| 78 | Journal of Clinical Epidemiology |
| 78 | Pharmacology |
| 75 | Genomics |
| 75 | Journal of Cellular Biochemistry |
| 75 | Journal of Investigative Dermatology |
| 75 | Journal of Medical Genetics |
| 75 | Journal of Medical Virology |
| 75 | Journal of Psychiatric Research |
| 75 | Nitric Oxide |
| 75 | Toxicology |
| 74 | Brain and Development |
| 73 | Cancer Immunology, Immunotherapy |
| 70 | Brain Injury |
| 70 | Cytogenetics and Cell Genetics |
| 70 | Glia |
| 70 | Journal of Biotechnology |
| 70 | Obesity Research |
| 69 | Immunopharmacology |
| 68 | Cellular Signalling |
| 68 | Immunology and Cell Biology |

TABLE 1-continued

| Score | Journal |
|---|---|
| 68 | Stem Cells |
| 68 | Stroke |
| 68 | Synapse |
| 67 | Immunology Letters |
| 65 | Cell Motility and the Cytoskeleton |
| 65 | Gene |
| 65 | Hormone Research |
| 65 | Journal of Cognitive Neuroscience |
| 65 | Journal of the Neurological Sciences |
| 65 | Pharmacological Research |
| 63 | American Journal of Physiology |
| 62 | American Journal of Medicine |
| 62 | Journal of Comparative Neurology |
| 60 | American Journal of Human Genetics |
| 60 | Cell Proliferation |
| 55 | Journal of Affective Disorders |
| 50 | DNA and Cell Biology |
| 45 | Anesthesiology |
| 41 | Biochemical Journal |
| 40 | Anesthesia and Analgesia |
| 40 | Biochemical Pharmacology |
| 40 | Cell Biochemistry and Function |
| 40 | Cell and Tissue Research |
| 40 | Cerebral Cortex |
| 40 | Experimental Cell Research |
| 40 | Histochemistry and Cell Biology |
| 35 | Journal of Dermatological Science |
| 20 | Chemistry and Biology |
| 20 | Genes, Chromosomes and Cancer |
| 20 | International Journal of Biochemistry and Cell Biology |
| 20 | International Journal of Biochemistry and Cell Biology |
| 10 | Archives of Biochemistry and Biophysics |
| 10 | International Journal of Antimicrobial Agents |
| 10 | International Journal of Cancer |
| 10 | International Journal of Experimental Pathology |
| 10 | Journal of Antisense Research |

Table 1, an exemplary look-up table for general rankings of biomedical journals.

while subject to a degree of subjectivity, these standards for ranking journals for their domain preferences are the same as those used by faculty-tenure review committee in major medical schools in the United States of America in order to evaluate the publication record of a tenure-candidate. Similarly, human experts in various domains recognize that certain information sources can have a pre-disposition to disregard or highly regard certain authors or types of submitted work. Since the editorial board and peer-reviewers of journals change with time, the tables for grading journals are not static but must be revised over time as reviewers or editors specific to domain specialties change. In combination with the Citation Index of impact journals, these criteria enable the scoring of a reference's support of gene's annotation.

Another variable used in the evaluation of the experimental support for an alleged role or function for a gene is a "follow-on" parameter. Reliable experimentalists often will publish a series of papers in reputable journals. They may publish on the same gene or encoded protein ("GeneRef" 230-a attribute of table "FollowOnWork" 230 in FIG. 7, or "ProteinRef" 230-b), a close homolog ("FamilyMemberRef" 230-c), another gene in the same pathway ("PathwayRef" 230-d) or the same gene or pathway in another organism ("altOrganismRef" 230-e). When a large body of work from an individual author or group of authors accumulates, then the probability of "truth" is high. In contrast, a single publication by an author that alleges unusual relationships amongst genes that fails to engender follow-on work (as roughly measured by the Citation Index) by the original author or others has a lower probability of "truth" which is reflected by a lower reference score ("RefScore" 200-k). An intermediate reference score occurs where a single publication triggers much work by other investigators, e.g. a high Citation Index but low "follow-on" value. Thus, this strategy compensates for the overall weakness of the Citation Index—by merely enumerating the occurrences of a referenced paper, the Citation Index may not be accurately represent the relatedness of subsequent work.

FIG. 7 depicts the functional annotative information stored for the genes according to an embodiment of the present invention. Database tables 160,170, 180, 190, 200, 210, 220, and 230 depicted in FIG. 7 include annotation information derived from peer-reviewed articles and other information accessed by server 14. A table of the annotation summary ("AnnotationSummary" 160) includes the sequence name ("SeqFile" 160-a), best hits ("BestHits" 160-b) which refers to the "DNAsequence" table 130 ("BestBlastnGID" 130-f), a link to the "Function" table 170 ("Function" 160-c), a link to the "Role" table 180 ("Role" 160-d), a link to the "Evidence" table 190 ("Evidence" 160-e). The Function 170, Role 180 and Evidence 190 tables contain many attributes which all refer to individual References ("Reference" table 200). Any reference in "Reference" table 200 ("RefID" 200-a) that supports the concept that a gene is an enzyme ("EnzymeRef" 170-a), a receptor ("ReceptorRef" 170-b), a channel or transporter ("ChannelRef" 170-c), a protein interactor ("InteractorRef" 170-d), a structural protein ("StructuralRef" 170-e), a nucleic acid binding protein ("NucleicAcidBindingProtein" 170-f), has a role in cognition ("CognitionRef" 180-a), or a role in development ("DevelopmentRef" 180-b), or a role in endocytosis ("EndocytosisRef" 180-c), a role in exocytosis ("ExocytosisRef" 180-d), or a role in Metabolism ("MetabolismRef" 180-e), or a role in regulation ("RegulationRef" 180-f), or a role in reproduction ("ReproductionRef" 180-g), or a role in signaling ("SignallingRef" 180-h), or a role in RNA splicing 0("SplicingRef" 180-i), or a role in vesicle trafficking ("TraffickingRef" 180-j), or a role in transcription ("TranscriptionRef" 180-k) is duly linked to the appropriate reference identifier ("RefID" 200-a). The weighted scores for each of these possible functions is stored as a multi-item list ("FunctionScores" 170-g). Similarly, the weighted scores for each of the possible roles is stored as a multi-item list; e.g. a "RoleScores" (180-l) equivalent to "0,100,100,0,0,0,0,0,0,0" might correspond to a single published article on a gene's role in the endocytosis of key nutrients during development in a prominent journal such as Science ("DevelopmentRef" 180-b and "EndocytosisRef" 180-c). In a database query, such a summary weighted score can be simply compared to other scores by both the maximum value of each comma-delimited item as well as the rank order amongst comma-delimited items. Similarly, any experimental evidence contained in the reference that shows that a gene's encoded protein was immune precipitated ("ImmunePrecipRef" 190-b), a gene's encoded mRNA was hybridized in a Northern assay ("NorthernRef" 190-c), a gene was hybridized in a Southern blot ("SouthernRef" 190-d), a protein band of appropriate predicted size was identified in a Western blot ("WesternRef" 190-e), an open reading frame was identified in a yeast two-hybrid interactor analysis ("InteractorAnalysisRef" 190-f), an enzymatic assay ("BiochemistryRef" 190-g), a pharmacological profile was determined ("PharmacologyRef" 190-h), a predicted homologous domain ("HomologyRef" 190-j) or a predicted structural 3-dimensional motif ("StructureRef" 190-k) is duly referenced to the appropriate reference identifier ("RefID" 200-a).

Referring further to FIG. 7, tables are shown to record the information about any pathway or reference. For any pathway ("Pathway" 210-a in table "Pathway" 210), a role may be assigned ("Role" 210-b), genes of the pathway listed ("GeneList" 210-c) and the location of the pathway identified ("Locations" 210-d). For any reference, a unique identifier ("RefID" 200-a) is recorded, the authors listed ("Author" 200-b), the article title ("Title" 200-c), the journal in which the article was published ("Journal" 200-d), the volume of the journal ("Volume" 200-e), the page numbers of the article ("Page" 200-f), the year of the article's publication ("Year" 200-g), and the reference score link ("RefScore" 200-k). The reference score link 200-k corresponds to the "RefScore" object/table 220 which also contains the reference identifier ("RefID" 220-a), the citation index value (if any) ("CitationIndex" 220-b), the topic field (e.g. immunology or neurobiology) ("Domain" 220-c), a domain weight-adjusted value for the journal quality, as described above, ("JournalRigor" 220-d), and the link to follow-on work table 230 ("FollowOnWork" 220-e). The follow-on table 230 consists of a reference to any subsequent work in which the same gene ("GeneRef" 230-a) or protein ("ProteinRef" 230-b), or homologous gene ("FamilyMemberRef" 230-c), or the same pathway ("PathwayRef" 230-d) or alternate organism ("altOrganismRef" 230-e) was studied by the original investigators.

5) Expression Profiling and Cluster Analysis

Referring back to FIG. 3, the present invention then obtains (step 59) and stores (step 60) expression profile data for the genes and their homologs. The expression profile data for a gene describes when and where the gene is expressed (i.e. transcribed to RNA). Profiles can be created for genes in cells or tissues under the influence of a drug; as a cell or tissue develops; during changes to the physiological state of the cell or tissue; in response to the development of disease in humans or an animal model; changes in response to a transgene or gene knock-out; and the like. For example, the expression profile data may indicate whether a gene is up-regulated/down-regulated during a stroke.

FIG. 8 depicts the gene expression profile data stored in the database according to an embodiment of the present invention. The four tables depicted in FIG. 8 correspond to a summary of the array result conditions ("ArrayResults" 240), the summarized array data ("ArrayData" 250), the details of the probe(s) ("Probe" 260), and the raw data ("RawData" 270). The array result conditions table 240 contains attributes that describe a unique experimental identifier ("ExptID" 240-a), the corresponding bar code ("BarCode" 240-b), the link for probe 1 ("Probe1" 240-c), the link for probe 2 ("Probe2" 240-d), a term that describes the grid pattern ("GridPattern" 240-e), the clone set identifier ("CloneSet" 240-f), the link to array data ("ArrayData" 240-g), and a comment ("Comment" 240-h). The array data table 250 contains attributes to describe the experimental identifier ("ExptID" 250-a), the name of the cDNA sequence ("seqFile" 250-b), the arithmetic mean of the background or normalized data ("Mean" 250-c), the standard deviation ("StdDev" 250-d), the ratio of any paired means derived from simultaneous application of two probes ("Ratio" 250-e), the time point at which the probes were made ("TimePt" 250-g), the biological state (e.g. diseased or normal) of the probe's mRNA origin ("State" 250-h), the clustering method ("ClusterMethod" 250-i), the cluster number ("Cluster" 250-j), the total number of clusters ("TotalClusters" 250-k), the cluster order pattern derived from the auto-regression analysis used in the causality analysis ("ClusterOrder" 250-l) and the date of the clustering ("ClusterDate" 250-m). Other attributes, such as patterns arising from ANOVA analysis or other parametric or non-parametric tests, and/or propagated error values may be added.

The probe data table 260 contains attributes for the probe identifier ("ProbeID" 260-a), the date of probe generation ("Date" 260-b), the type (first strand cDNA or double-stranded cDNA) of probe ("Type" 260-c), the biological model ("Model" 260-d), the identifier for the preparation of RNA ("RNAprep" 26-e), the labeling (radioactive or fluorescent) method ("LabelType" 260-f), the time point at which the RNA was collected ("TimePt" 250-g), the biological state of the probe's mRNA origin ("State" 250-h), and a comment ("Comment" 260-i).

The raw data table 270 contains attributes for the experimental identifier ("ExptID" 270-a), the sequence name ("seqFile" 270-b), the probe name ("Probe" 270-c), the raw intensity value ("RawValue" 270-d), the local background or normalization factor ("LocalBgnd/factor" 270-e), and the arithmetically corrected intensity value ("CorrectedValue" 270-f).

Referring back to FIG. 3, the present invention then performs clustering analysis on the behavior of DNA sequences in expression profile studies (step 62). According to clustering analysis, data complexity is reduced by partitioning the genes into groups or "clusters" that have similar attributes. These attributes can be the behavior of genes monitored over multiple time points in response to an injury, onset of disease or altered physiological state (e.g. intensity or ratio of intensities resulting from hybridization of a gene set with probes derived from normal and diseased tissue). Also, these attributes can simply be the response of genes from cells, tissues or animals treated with multiple concentrations (e.g. 5, 6 or 7 concentrations) of many drugs (e.g. 10, 100, 1000 or 10,000) with differing mechanisms of action at a single time point. These attributes can also be the response of cells or animals subjected to many altered physiological states (e.g. elevated or diminished nutrients, ions or temperature, transient ischemia, shock, anxiety, enriched environment, discomfort or depression) or genetic states (e.g. transgenic or gene knock-out animals) monitored at a single time point relative to untreated cells or tissues. The result of clustering gene expression data is clusters of genes with similar expression profiles.

An embodiment of the present invention implements a method of gene clustering that is tuned to the simplified, yet specific nature of the array data itself. In order to reduce data complexity, many clustering methods have been applied to gene expression profile data: these include hierarchical, K-means, self-organizing maps (Tamayo et al. PNAS 96:2907–12), or support vector machines (M. Brown et al. PNAS 97:262–7). An embodiment of the present invention uses a K-means distance with Euclidean distance or other distance metrics (provided by Partek of St. Louis Mo.) because of its ability to efficiently cluster data in an automated unsupervised manner. One of the common criticisms of K-means clustering is that the number of clusters must be determined a priori. However, the present invention uses the Davies-Bouldin algorithm (IEEE Transactions on Pattern Analysis and Machine Intelligence, Vol. PAM1-1, April 1979) which determines the optimal number of clusters based upon the dispersion and flatness of clusters.

According to an embodiment of the present invention, the present invention clusters the genes based on time-course data, as described by the expression profile data. According to a specific embodiment of the present invention, packages provided by Partek Inc. and/or SAS Institute, Incorporated of Cary, North Carolina may be used to perform the clustering analysis. For time-course data, the clustering analysis may also include causality analysis to predict ordered relationships between clusters on a time basis. Causality analysis is performed using an auto-regressive and auto-correlative method using software packages such as the Statistical Analysis Software from SAS Institute, Incorporated. The results from the clustering analysis are stored in a database (step 64). The cluster analysis results are inserted into the array data table 250 of FIG. 8: for each gene ("seqFile" 250-b), the clustering method ("ClusterMethod" 250-i), a cluster number ("Cluster" 250-j), the total number of clusters ("TotalClusters" 250-k), and the cluster order ("ClusterOrder" 250-l).

The type of clustering method(s) used to analyze array data may be selected based on factors such as a priori knowledge about the behavior of the immobilized genes; the composition of the gene set itself; the choice of array technologies, etc. Array technologies take different forms, for example cDNA and oligonucleotide arrays, etc. Since the oligonucleotide arrays can have a higher density than cDNA arrays, an effort has been made to increase the number of sequences per unit surface area in order to gain thoroughness. Thus, many array chip designs seek to deposit large numbers of nucleotide sequences per chip, e.g. species-specific chips (mouse, rat or human chips from Affymetrix, Santa Clara, Calif.); genes representative of a field (apoptosis, cancer or neurobiology chips) and the like. However, analysis of such chips can be complicated by the fact that many sequences or polynucleotides on the chip are irrelevant to the biological system being studied.

In one embodiment of the present invention, the analysis of gene clusters is simplified by the use of immobilized groups of polynucleotides that are disease- or physiology-specific, or clustered in a biologically relevant group. Such collections of genes can be generated, for example by a method that enables the identification of genes expressed at a measurable level higher in one state than another. For example, in tumors or animals subjected to ischemia, those skilled in the art of molecular cloning can identify and isolate cDNA clones and derive the sequences thereof for genes whose expression is elevated 2, 3 or 10 fold higher in the altered physiological state; e.g. differential display and subtractive cloning are two such methods. Examples of genes and groups of genes are identified in co-pending U.S. patent application Ser. No. 09/627,362, filed on Jul. 28, 2000. The number of disease-related or physiologically-related genes may range from about 1000, about 6000, about 10,000, or about 20,000 per chip.

When analyzed by principal components analysis, typically up to 90% of the variability in the gene expression profile data generated by arrays of 6000–10,000 disease- or paradigm-specific gene targets can be explained by the first 3 principal components or eigenvectors. With a large number of genes unrelated to the biological paradigm of the probe (e.g. 40,000–60,000 genes present on some general arrays), the data variability is likely explained by many more principal components, which makes it difficult to analyze more than any 3 of all principal components in 3-dimensional space. For analysis of such general array data, other clustering methods might be more appropriate, such as hierarchical clustering, although optimal hierarchical clustering is highly iterative and false clusters are often generated.

In order to infer the time-order of gene clusters derived from the above, it is possible to calculate likely causality by a moving auto-regressive analysis. A time-order is a linear ranking of clusters by a deduced set of relationships ordering the first possible cluster relative to other clusters in an iterative process. A biological example of this problem is the goal of understanding which genes respond earliest to an injury or infection, followed by the elucidation of time of activation of subsequent, related or unrelated genes. A ordered set of clusters from expression profile data is achieved initially by selecting a representative subset of genes near the centroid of each cluster (e.g. 2, 5 or 10 representing about 1–10% of the total number of genes) and performing a moving auto-regressive test against the remaining genes of the monitored population of genes (e.g. 2, 5 or 10 genes compared to all 6000 or 10,000 genes) from all clusters (Statistical Analysis Software of SAS Institute, Incorporated, Cary, N.C.). The ranked order of clusters is stored in "ClusterOrder" (**250-*l*) in step 64**.

The accuracy of ordering clusters is dependent on the completeness of the calculation, but calculation of cluster order is computationally intensive. For example, according to a specific embodiment, the above calculation, for example requires about 24 hours on a standard single CPU Unix workstation with 1 gigabyte of RAM; e.g. a Sun Ultra10 workstation with 300 MHz CPU. This time-series analysis is only applicable to datasets with regularly spaced time-points (e.g. 10, 20 or 40 instances spaced 30 min, 1 hr or 3 hrs apart). The time-resolution of the causality analysis is dependent upon the density of intervals over the entire course experimental course. For the highest resolution of time-ordered relationships amongst clusters, 20, 50, or 100 time-points are preferable. For the highest accuracy amongst clusters, a comprehensive auto-regression is calculated provided sufficient computer power (e.g. 6000 genes compared to 6000 genes or 10,000 genes compared to 10,000 genes requires supercomputer ability or the efforts of a cluster of workstations such as a Beowulf cluster).

6) Obtaining Pathway Information

The computer-implemented methods of this invention employ information extraction techniques to generate summarized information about the biological relationships between genes in a list of genes. A goal of these methods is to automatically and systematically generate and present summarized information about the biological relationships between the genes of a list. Without these methods, users typically spend considerable time manually searching databases to find information about a particular gene and its relationships to other genes before the particular gene product can be developed as, e.g. a drug target, a therapeutic protein etc.

Referring back to FIG. 3, after the clustering analysis, the present invention obtains pathway information regarding the biological relationships between genes in a list, the list representing a cluster or any other group of genes of interest. Pathway information can be accessed from public databases such as MEDLINE, OMIM and the U.S.P.T.O. patent databases through information retrieval and extraction procedures. Pathway information can also be gathered from pathway databases such as the Kyoto Encyclopedia of Genes and Genomes (KEGG) or the Munich Information Center for Protein Sequences (MIPS), as described earlier. One embodiment of the invention is that data from a public databases are downloaded to a private network, thus providing a set of internal data.

The determination of biological relationships is normally carried out in three steps. Firstly literature relevant to genes in a list of genes is identified, downloaded and stored. Second, information regarding relationships between two or more gene products is extracted from the literature using information extraction techniques, and third, this information is cross referenced and a graph is built to display the cross-referenced information. Typically the data produced from these steps, such as a list of interactions, and a directed graph, is stored in the expert database 4 and is available for viewing along with gene expression data, allowing the user to quickly determine whether gene expression results are meaningful, based on other evidence in the public database 17, extracted and summarized by these procedures.

In one embodiment, the automated extraction, processing, cross-referencing and presentation of information regarding the biological relationships of genes and gene products, or other products requires retrieval of a collection of journal articles by word search, performing natural language processing (NLP) and information extraction, saving a list of interactions, cross-referencing the interactions and visualizing the cross-referenced interactions. Within NLP, several processes may take place. Tokenization pre-processes text into words and phrases, separated by white space and punctuation. Stemming is used to find and standardize variations of the same word, for example converting "regulation of" to the stemmed form "regulate", using the SPECIALIST Lexicon medical vocabularies of the National Library of Medicine's Unified Medical Language System (UMLS; Humphreys (1998) J. Am. Med. Inform. Assoc. 5, 1–11). Finally tagging algorithms annotate the tokenized and stemmed text with parts of speech (i.e. syntactic) or class (semantic) information to define nouns, verbs, adjectives and any other parts of speech, and the classification of the words. The combination of syntactic tagging and semantic tagging can further determine which nouns are the subject of which verbs. Tagged text is then presented to information extraction algorithms.

Information extraction systems may recognize noun phrases that contain verbs of interest (e.g. Sekimizu (1988) Genome Inform. Ser. Workshop Genome Inform. 9, 62–71). For example, a system may identify the verbs activate, bind, interact, regulate, encode, signal and function, any other word used to describe interactions commonly found in MEDLINE abstracts, such as those described by Stephens et al (Pac Symp Biocomput. (2001) 483–95) or any other word that can describe interactions found within the SPECIALIST Lexicon medical vocabularies of the National Library of Medicine's UMLS (Humphreys (1998) J. Am. Med. Inform. Assoc. 5, 1–11). This system finds noun phrases that are contained within phrases or sentences with one or more of the specified verbs. A parser using supplied rules, comprising 1) the specification of semantic and syntactic components, 2) specification of the output form if the supplied rule is successful and 3) a system for assigning a quality score or grade based on how well the input fits the rules. The output from such an information extraction system may be X interacts with Y, or Y regulates Z. With the addition of nested actions, modifiers of objects and actions, relations between actions, relative clauses and conjunctions to template recognition and HMM models, more complicated relationships can be determined, for example, X interacts with Y in cancerous cells.

Once the relationships between genes have been determined, they can be displayed in the form of a directed graph. Several different graphing programs and algorithms can be used for generating directed graphs, as is known by one of skill in the art, for example those described and referenced by Becker (Bioinformatics 17: 461–467 and references therein). One suitable graphing tool is the Java applet for visualizing protein-protein interactions developed by Mrowka (Bioinformatics (2001) 17: 669–670). The applet is based on the Graph.Java applet distributed in the Java development distribution of SUN Microsystems. A directed graph is displayed on FIG. 12. The thickness, color, texture and/or transparency of the graphical links (edges) between the genes (nodes) may represent a confidence, based on the rankings of journals providing the information extracted, that the interaction is a real biological phenomenon.

Figure 9:
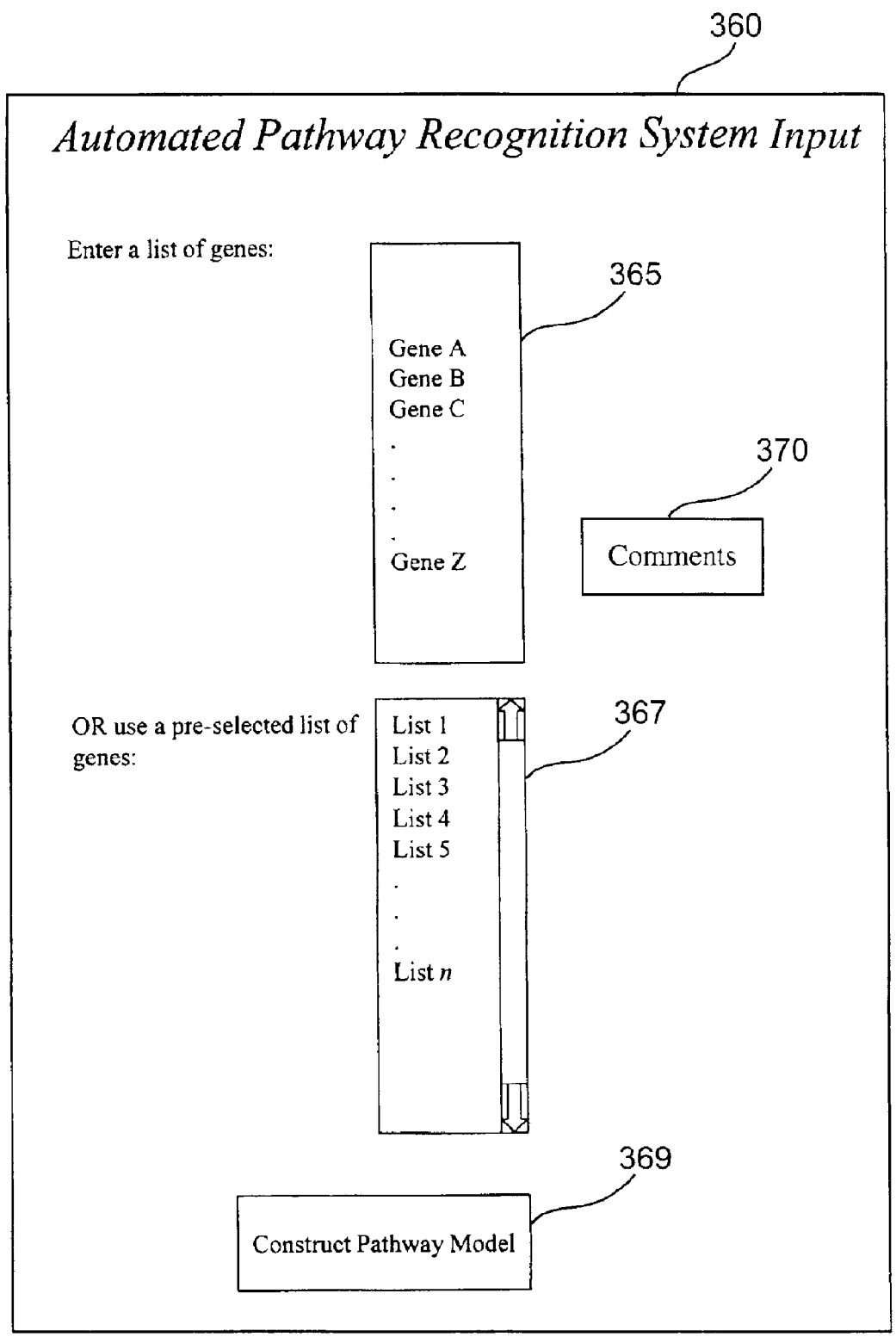
FIG. 9 depicts a client input interface.

A diagrammatic representation of an input graphical interface into which a user enters a list of genes in one embodiment of the invention is shown in FIG. 9. User inputs a list of genes, preferably through an input graphical user interface of a client machine 16-1 and 16-2. Web browser 360 displays fields for hand entry of a list of genes 365, a field for comments 370 and means for identifying a previously made list of genes 367, for example an output list of genes from a clustering algorithm wherein the genes in a list of genes form a cluster, either selected from the gene expression database or selected by a user. Optionally, the system may automatically extract information from lists of clustered genes stored in the database, without input from the human user. User interface 360 also includes a button, or other means, for initiating the execution of the described pathway model construction methods. The input information about a gene could be a seqFile number 160-a, a BestHits name 160-d, or any other identifier or key that can link the input gene information with a particular sequence or particular gene name through the DNA sequence database 130 or the annotation summary of the expert database 160. In one embodiment, the user inputs a list of gene names 305, in another embodiment the user enters a list of seqFile identifiers, and in another embodiment, the user enters a list of other identifiers that can be corresponded to seqFile identifiers using a conversion table. If user has put in a list of identifiers that correspond directly or indirectly to a seqFile number (160-a), a query will be used to extract names for genes represented by the input list. The name of the gene can be extracted as the BestHits field (130d) of the DNA sequence database (130) or the BestHits field (160-b) of the annotation summary (160).

Figure 10:
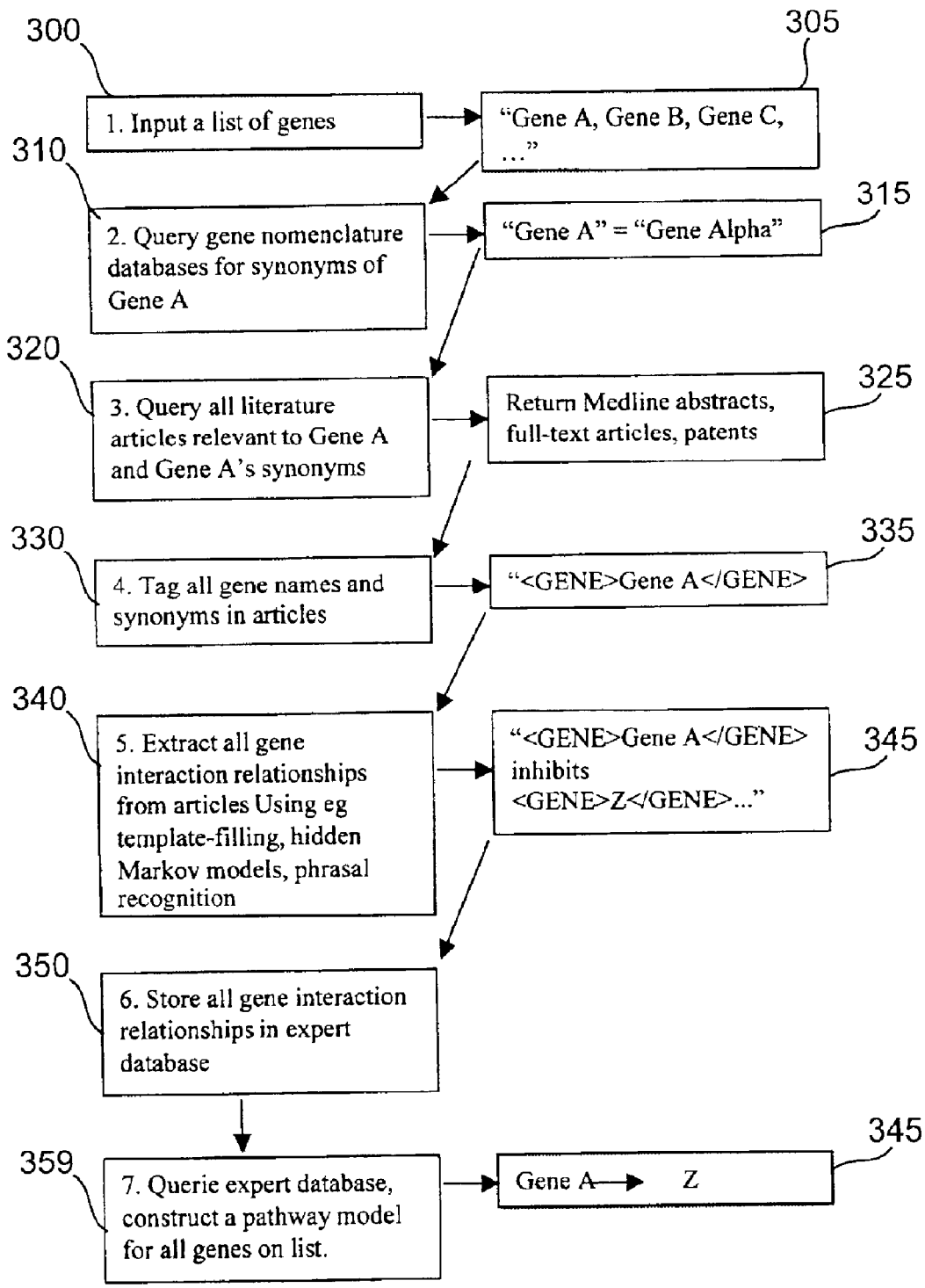
FIG. 10 a simplified flowchart showing processing performed by an embodiment of the invention to obtain pathway information about genes on a list of genes.

FIG. 10 is a diagrammatic representation of how pathway information is extracted for genes in a gene list. Once a list of genes has been prepared and entered into the client machine (300), a list of gene names is prepared (305) and a gene nomenclature database is queried to identify and extract synonyms for each gene name on the list (310). Lists of synonyms can be obtained through the Human Genome Organization (HUGO) or SWISS-PROT databases, or the GeneCards synonym database of the Weizmann Institute. In this example, gene A is also called gene alpha, according to a nomenclature database (315). Typically this lookup list of gene names and synonyms will be represented as a table in a database on server 14, that is capable of being queried. The table of gene names is used to query suitable databases to identify literature articles relevant to the gene name or its synonym (320). In one embodiment, a keyword and boolean search is performed using Hypertext Transfer Protocol (HTTP) using the NLM MEDLINE abstracts via an HTTP URL, which allows for download of groups of abstracts and other literature from the National Library of Medicine website. Optionally a sophisticated information retrieval algorithm could be used to query for, rank, and download groups of articles from a database. The method for identifying and downloading relevant articles is often particular to a specific literature database, and an application programming interface (API) may also be used, as is known to one of skill in the art. For example MEDLINE, MEDLINE abstracts, the U.S.P.T.O. patent databases and the WIPO patent database are queried and the full-texts or abstracts of articles, patents, and other relevant literature are retrieved (325) and stored on server (14).

After all relevant literature has been down-loaded and stored as text files, gene names and their synonyms are tagged (330). Tagging is a means by which words, in particular nouns and verbs, are labeled within larger bodies of text. In one embodiment, genes names found within the HUGO curated list of gene names, the SWISS-PROT list of protein names the Galton Library of the Medical Research Council, UK, or any other gene, chemical, process, or agent listed in the UMLS can be used for tagging. In a particular example (335), the tagging mechanism, using Extensible Markup Language (XML), gene names are labeled by placing "<GENE>" before the gene name and </GENE> after the gene name. In a body of text, Gene A would be labeled as follows: <GENE>GeneA</GENE>. Several different methods of tagging can be used in information extraction, as is known to one of skill in the art. An example of an exact match tagging algorithm is the Marmot program, developed by the University of Massachusetts.

Once gene names are tagged within the downloaded text files, information regarding biological relationships is extracted from the text files (340). Information extraction may require a list of words that describe interactions between a supplied list of nouns. Verbs used to describe the interactions between different genes can be "activate", "associate", "interact", "bind", "inhibit", "regulate", "up-regulate", "down-regulate" or "complex", however any verbs describing relationships as listed in the UMLS, any verb commonly used in the MEDLINE database, or any other useful verb can be used.

Information extraction relies on such techniques as template filling and Hidden Markov Models (340), although several other techniques for information extraction are known to one of skill in the art. An exemplary list of templates used in the preferred embodiment are as follows: "Gene A can activate Gene B . . . ", "Gene A is associated with Gene B . . . ", "The interaction of Gene B and Gene A, . . . ", "Gene A binds to the N-terminal domain of Gene B, . . . " and "Gene B induces inhibition of Gene A in . . . ".

The output of information extraction in this example is a summary of an interaction between two genes, for example "Gene A inhibits Gene B" 345 wherein two genes interact by an interaction type, in this case the type is inhibits. Further phrasal recognition and templates examples can be used to develop more complex relationships, for example "Gene A inhibits Gene B in particular conditions", for example in cancer, or when Gene A gene product has been phosphorylated. In one embodiment of the present invention, information extraction is performed by one or a combination of the techniques of template filling, Hidden Markov Models and phrasal recognition. Information extraction may also employ text comparison algorithms such as BLAST, Teiresias or Swith-Waterman to identify phrases or words that are similar to phrases or words of interest.

Template-filling is a NLP technique which utilizes domain-specific rules for information extraction. A template defines a set of rules that syntactically and semantically generalizes slots or positions and relations of words or word phrases. For example, a simple template may define the rule to extract "Gene A", "inhibit", and "Gene B" from the phrase "Gene A can inhibit Gene B." The template may be defined as "[noun (GeneName)] [verb phrase (Interaction Verb)] [noun (GeneName)]." The slots of the rule are contained within the brackets. The syntax of the rule is defined by (1) the grammatical order and (2) the part-of-speech of the slots. The semantics rules are defined within parentheses of each slot brackets, ie "GeneName" and "InteractionVerb." The complexity of templates can vary depending on the complexity of the syntactical and semantic structure of phrases from which information is being extracted. Ultimately, a group of templates can be used to match and extract information from domain literature.

Markov models and Hidden Markov models (Bernard Merialdo (1994).

Computational Linguistics 20(2):155–172), or HMMs, are finite-state, statistical models of random sequences. In NLP, HMMs can be used to model a sequence of words or phrases by defining a set of states, ie words, and probabilities of movement between states, ie syntactic or semantic rules between the words. HMMs can be trained to probabilistically match a specific set of sentences. A trained HMM can be used to extract the best states matched in a sentence, ie underlying words and phrases, and probability of match.

Machine learning algorithms, such as the C4.5 decision tree algorithm, are another type of extraction NLP technique. The University of Massachusetts. CIIR "Badger" tool utilizes trained decision trees to extract information from text. Decision trees utilize a branching structure of states to define a set of cascading rules by which information can be extracted. Decision trees are trained with a syntactically and semantically tagged set of sentences to generalize their structure to optimally extract information. Neural networks are another example of machine algorithm used for information extraction in NLP (B. Widrow, D. Rumelhart, and M. A. Lehr. Neural Networks: Applications in Industry, Business, and Science. Comm of the ACM, volume 37, number 3, pages 93–105, March 1994).

Using information extraction techniques such as those described above, a list of biological interactions is created and stored 350 in a database. This list comprises many pairs of interactors, for example Gene A and Gene B, and an interaction type associated with the pair, for example, "inhibits" 355. Other information, such as the source of the information, for example a journal citation and/or the author list, can also be stored with the interactions. As a final step in the information extraction process the stored relationships for all tagged genes is queried with the original input gene list 365 and a table is created describing only those interactions that involve a gene name or its synonym on the original input gene list 365. This process may be iterative, in that the interactors of genes on an original input gene list may be used to populate another input gene list, and the process can be initiated again. In this embodiment, relationships between distantly-interacting genes can be identified.

Figure 11:
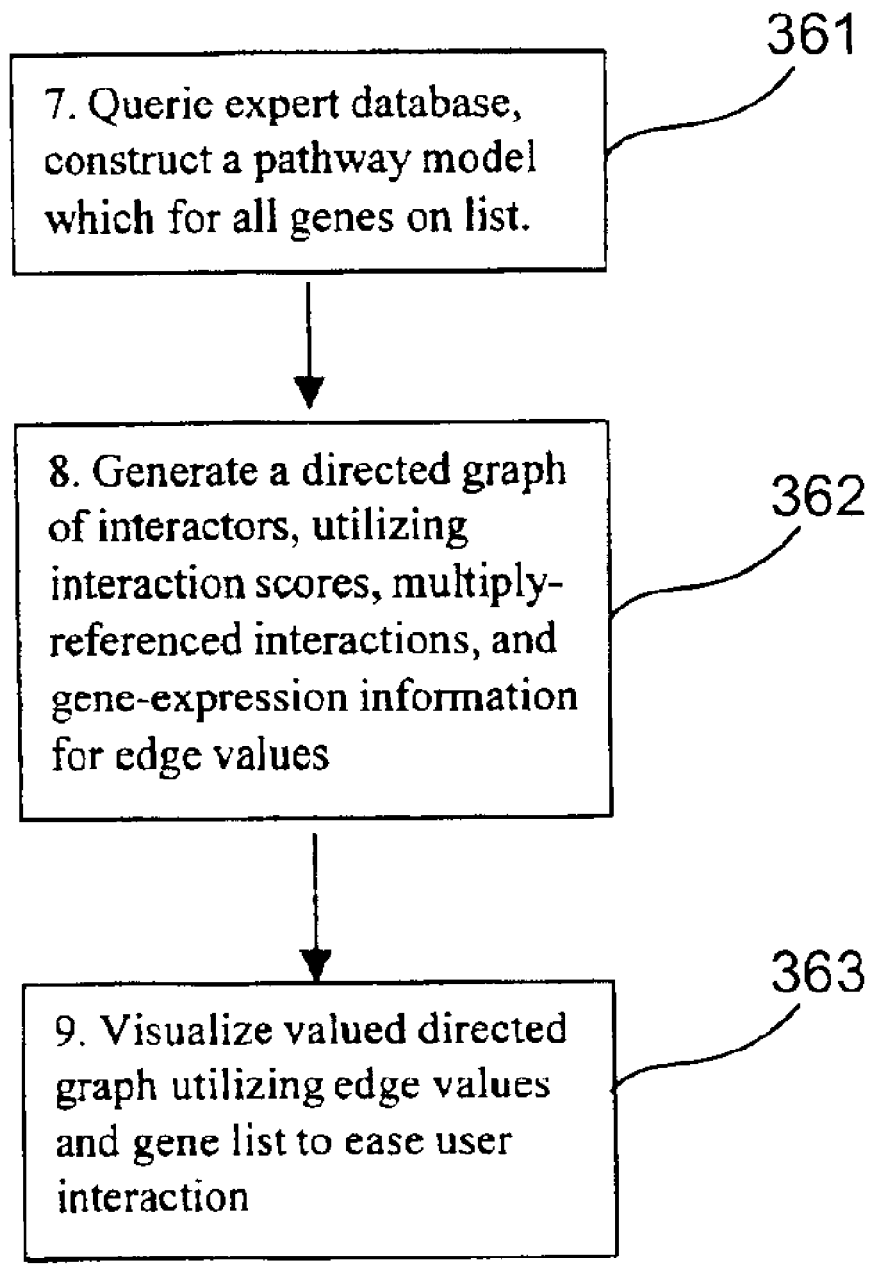
FIG. 11 is a simplified flowchart showing how directed graphs are produced to represent pathways of gene interactions.
Figure 12:
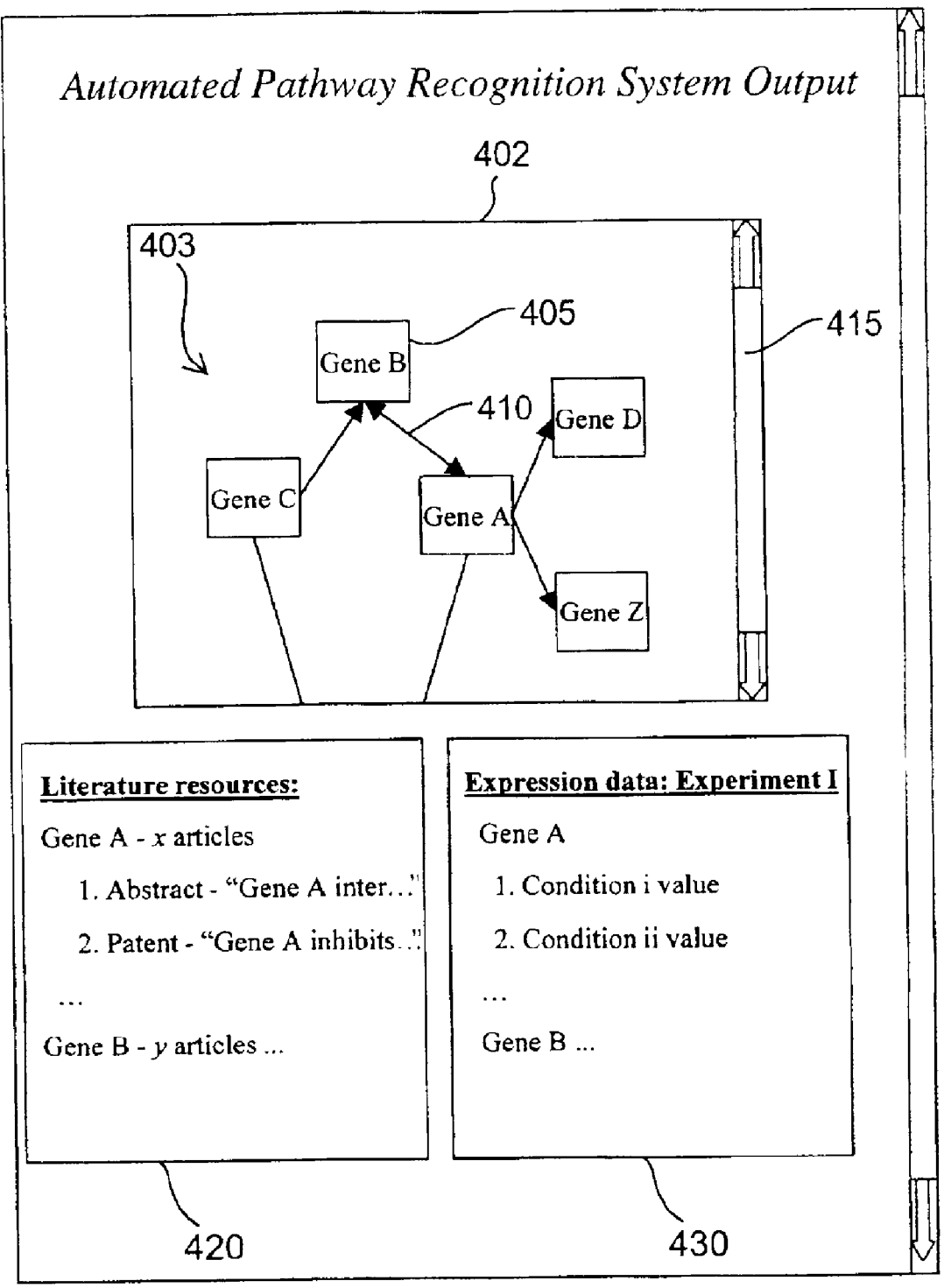
FIG. 12 depicts a client output interface.

The table describing interactions involving gene names on the original input gene list can be presented to the user in many ways, including as a simple table, a two-dimensional interaction matrix, or many different types of graphs. In FIG. 11, a pathway model is constructed 361 and a directed graph is generated 362 and visualized 363. A graphical display of the output user interface is shown in FIG. 12. Web browser 400 contains three windows, a window 402 showing a directed graph 403 with a scroll bar 415, a window 420 showing literature corresponding to an interaction, and a window 430 showing gene expression information derived from gene expression profiling experiments. Thus, gene expression data for a group of genes or DNA sequences can be viewed simultaneously with a graph of interactions between a group of genes or DNA sequences.

The preferred method for presenting this interaction information to the user is by cross-referencing the interaction information and generating a directed graph 403, wherein a gene can be represented by a node 405, and the relationship is represented by the edges of the graph 410. The nodes are typically labeled with the gene name; and an edge value, corresponding to the strength of the interaction, can be used to label the edge. The edge may optionally be labeled with the relationship, and hyperlinks leading from the edges can be used to download, via a query of the expert database, information such as the abstracts and publications that were used to establishing the relationship.

Graphing algorithms may typically take into consideration interaction scores based on citation indexes scores or author scores, as described above, and how many times a particular reaction has been referenced for edge values. Gene expression information can also be taken into consideration in the calculation of edge values, for example if two genes are co-regulated according to data in the gene expression database, the edge value for a relationship between these two genes may be higher. Graphs are stored in the expert database for viewing by a user. In a preferred embodiment, the graphs are dynamically generated per user request, in order to incorporate updated data.

Figure 13:
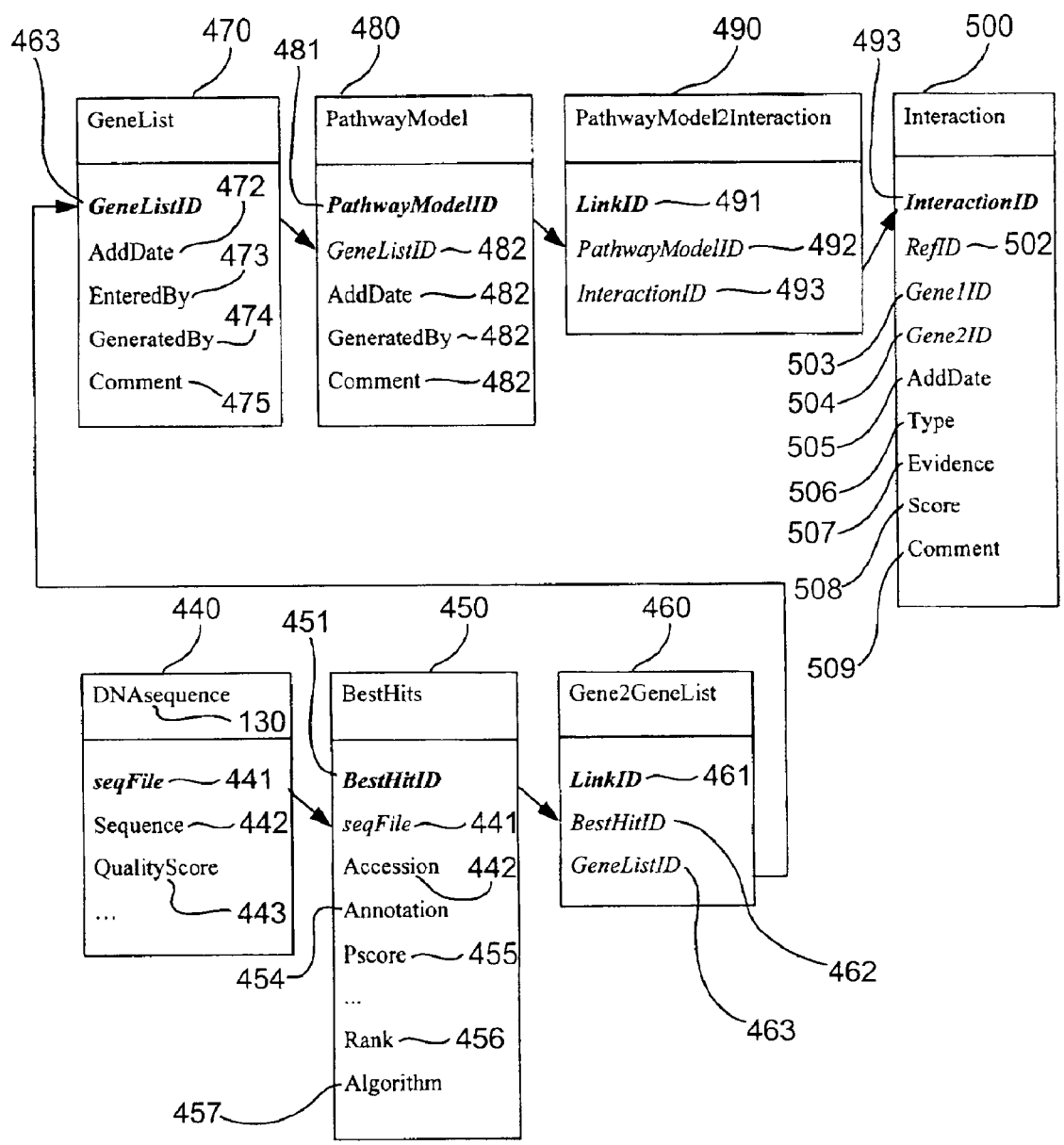
FIG. 13 depicts a relational database schema for addition to the expert database showing pathway information stored for genes according to an embodiment of the invention.

In one embodiment of this invention, the process of gathering and presenting information regarding the biological relationships between genes produces several tables that can be part of the expert database. A simple schema diagramming these tables, the relationship between these tables, and how the tables are linked to the expert database of FIG. 7, is shown in FIG. 13. One of skill in the art would recognize that there are several schemas for such a set of tables.

The process is initiated when the user inputs a list 440, usually of seqFile Ids 441 (160a from FIG. 7), into the input interface of a client machine. Querying the BestHits table 450 using a seqFile ID 441 returns the BestHitID 451 or BestHitIDs corresponding to the given seqFile ID 441. For a given seqFile ID, zero, one or many BestHitIDs can be obtained via this query. The Accession number 453, Functional Annotation 454, Pscore 455, Rank 456, and Algorithm 457 for each BestHitID 451 are also obtained via query of the BestHit table 450. The BestHitID 451 with the highest Rank for a seqFile ID 441 is entered into a Gene2GeneList table 460 that contains at least two fields: the BestHitID 451 and the GeneListID 463, a unique ID that has been assigned to each list of genes by the database management system. This process, of obtaining the BestHitID 462 with maximal Rank for each seqFile ID 441 and filling the Gene2GeneList table 450, is repeated for each seqFile ID in the input list 440. In the GeneList table 470, other information about the list of genes, keyed by GeneListID 463, such as the date 472

(AddDate), who entered the list 473 (EnteredBy), the method by which the list was generated 474 (GeneratedBy) and additional comments 475 (Comment) can be entered. After the GeneList table 470 has been populated, the information retrieval and information extraction processes are carried out for all genes associated with a particular input list, and each process produces a pathway model. Each pathway model is assigned a unique ID by the computer, PathwayModelID 481, and information such as the input list to which the model corresponds 463 (GeneListID), the date performed 483 (AddDate), how the pathway was generated 484 (GeneratedBy) and general comments on the pathway 485 (Comment) are stored in the PathwayModel table 480. The PathwayModel2interaction table 490 defines the interactions of a pathway model using the PathwayModelID 481. For a given PathwayModelID 481, zero, one or more InteractionIDs 493 may exist in the PathwayModel2interaction table 490. The unique InteractionID 493 links to the Interaction table which identifies a literature-referenced 502 (RefID), gene-to-gene (Gene1ID 503, Gene2ID 504) interaction, added on a date 505 (AddDate), the interaction type 506 (Type), specific experimental evidence 507 (Evidence), confidence in the experimental evidence 508 (Score) and a general comment 509 (Comment) are stored in the Interaction table. In a further embodiment of the invention, a plurality of BestHitIDs 451, are used to generate various pathway models. A further embodiment would utilize not only gene-to-gene interaction data, but also utilize gene-to-disease, gene-to-pathway, gene mutation, and gene knockout data to define pathway models.

7) Using the Expert Database

The information stored in the database according to the present invention facilitates the identification of candidate genes (step 68 in FIG. 3). Identification of candidate genes results from the viewing of gene expression information in combination with the function(s), role(s) and/or pathway(s) information about groups of genes. The reference score-based assignments for either majority or minority view annotations of function(s), role(s) and/or pathway(s) enables the identification of new or serendipitous relationships. Such biological novelty, i.e. the unexpected up- or down-regulation of a gene in the context of an existing or new pathway, can be one of the hallmarks of candidate genes. For example, in a signaling pathway, study of a disease model may reveal that one, two or three known phosphodiesterases are up-regulated in the context of a pathway not normally characterized by those enzymes. Or, a new family member of this enzyme class might be discovered to be up-regulated along with the expected enzyme. Both are examples of candidate genes revealed by the combination of annotated DNA sequences and expression profiling data—particularly if the published literature contained an obscure reference to such a relationship under abnormal circumstances dissimilar to the conditions of the experimental paradigm. The latter result would be significant due to the redundancy of biological systems. Conversely, if 7, 8 or 9 of 10 genes of a well known pathway are found to be up-regulated in a disease or injury model (as determined by a comparison of all pathways of each gene expression profile cluster), then the 1, 2 or 3 genes that failed to be induced (as determined by a query comparison to the pathway database) might also be considered candidate genes. In this example, the user might conclude that a new inhibitor is blocking the 1, 2, or 3 missing genes and hence blocking the inhibitor might diminish the pathology or improve recovery. The user might then search for known or postulated inhibitors of any member of the pathway.

The information stored in the database may be accessed or queried by users interested in identifying candidate genes. According to a specific embodiment, the present invention provides an interface allowing users to specify a query including criteria characterizing candidate genes. In response to the user query, the present invention searches the database to identify genes which satisfy the user-specified search criteria. A typical search might examine the group of classified genes (e.g. by function, role or pathway) appearing in an early or middle expression cluster (based on "Cluster" 250-$j$ and "ClusterOrder" 250-I). By comparing the similar attributes (e.g. a query of the type "what apoptotic regulator genes are present in early clusters along chemokine genes?") within upstream or downstream clusters, the user may be able to deduce, for example, that the apoptotic pathway in a particular infection model of immune cells was altered by either (a) the appearance of a new apoptotic regulator gene or chemokine at an unexpected time or cluster, or (b) the absence of altered expression for a gene known to be induced in the pathway. Alternatively, the user might query what low-likelihood roles or pathways might explain the presence of a given class of receptors. In response to the user query, the present invention uses the user-specified query criteria to search the information stored in the database and outputs genes which satisfy the user-specified search criteria by either their presence or omission from either known or low-likelihood roles (or pathways) or lists of genes with known function(s) or role(s). In this manner, the information stored for the plurality of DNA sequences and their behavior in expression profile data facilitates identification of candidate genes.

A particular use for the expert database described above is to allow users to quickly access information regarding biological relationships of genes that have been clustered together by their pattern of expression. This information may allow a user to be more confident that a particular gene is involved in a particular process, which will facilitate the selection of that gene as a target for future therapies or treatments. Because of the size of the public literature databases, in particular the MEDLINE database, it may take a researcher several hours, or in many cases, days to laboriously research the possible interactions between genes of a group of genes to identify which of them can be promoted as a candidate. The methods of this invention are computer-implemented and requires very little of the investigator's time and energy e.g. to input a list of genes or sequence identifiers, and allow the researcher to view this data in a summarized, organized, and cross-referenced format. While the computer is analyzing data according to the user's request, the user can focus on other matters. Users can alter the confidence scoring of the interactions or pathway models, which influences the analysis of interactions and pathway models in future analyses.

A feature of the present invention is that it provides support for both intra-and inter- time-resolved gene cluster components; i.e. between or amongst genes in subsequent or previous groups of genes. Thus, a human expert can choose from a palette of options to refine a first iteration of gene network or pathway building. The parameters in turn can be used to recalculate the likelihood of other annotations and pathways to explain the behavior of a single gene, group of genes, or cluster of genes. Collectively, these methods can reduce the number of differentially regulated genes to a smaller group; from which candidate genes can be chosen by the human expert.

Although specific embodiments of the invention have been described, various modifications, alterations, alternative constructions, and equivalents are also encompassed within the scope of this application. The described invention is not restricted to operation within certain specific data processing environments, but is free to operate within a plurality of data processing environments. For example, although the present invention has been described in a distributed computer network environment, the present invention may also be incorporated in a single stand-alone computer system. In such an environment, the same stand-alone computer has access to the various biological databases according to the present invention and may act both as a client and a server. Additionally, although the present invention has been described using a particular series of transactions and steps, it should be apparent to those skilled in the art that the scope of the present invention is not limited to the described series of transactions and steps.

Further, while the present invention has been described using a particular combination of hardware and software, it should be recognized that other combinations of hardware and software are also within the scope of the present invention. The present invention may be implemented only in hardware or only in software or using combinations thereof.

The specification and drawings are, accordingly, to be regarded in an illustrative rather than a restrictive sense. It will, however, be evident that additions, subtractions, deletions, and other modifications and changes may be made thereunto without departing from the broader spirit and scope of the invention as set forth in the claims.

What is claimed is:

1. A computer-implemented method of identifying candidate genes from a plurality of DNA sequences, the method comprising:
   obtaining gene expression profile data for a plurality of DNA sequences, wherein the gene expression profile data describe behavioral patterns of gene expression;
   identifying a group of DNA sequences for further analysis;
   using information extraction algorithms to retrieve and extract pathway information from a database related to the group of DNA sequences;
   cross-referencing said pathway information to said DNA sequences;
   ranking the pathway information based on a ranking of a publication in a citation index;
   viewing said cross-referenced information and said ranking; and,
   wherein viewing the cross-referenced information and said ranking facilitates the identification of candidate genes.

2. The computer-implemented method of claim 1, wherein the pathway information is stored in a database.

3. The computer-implemented method of claim 2, wherein the cross-referenced information is stored in a database.

4. The computer-implemented method of claim 1, wherein the cross-referenced information is viewed as a directed graph.

5. The computer-implemented method of claim 1, wherein identifying a group of DNA sequences further comprises clustering the gene expression profile data to form clusters.

6. The computer-implemented method of claim 5, wherein clustering is unsupervised clustering.

7. The computer-implemented method of claim 5, wherein clustering is supervised clustering.

8. The computer-implemented method of claim 5, wherein clustering is a combination of supervised and unsupervised clustering.

9. The computer-implemented method of claim 5, wherein the group of DNA sequences represents a cluster.

10. The computer-implemented method of claim 1, wherein the gene expression profile data is derived from microarray experiments.

11. The computer-implemented method of claim 1, wherein the information extraction is performed using natural language processing algorithms.

12. The computer-implemented method of claim 11, wherein the natural language processing algorithms include template filling or Hidden Markov-Models.

13. The computer-implemented method of claim 11, wherein an information extraction algorithm utilizes a text comparison algorithm.

14. The computer-implemented method of claim 1, wherein the information is extracted from one or more literature databases from the group consisting of MEDLINE, USPTO patent published patent database, USPTO issued patent database, the WIPO patent database, and the KEGG, MIPS and OMIM database.

15. A data processing system for identifying candidate genes from a plurality of DNA sequences of known expression pattern, comprising:
   a processor; and,
   a memory coupled to the processor, wherein the memory has instructions for execution by the processor, the instructions comprising:
      instructions for accessing and extracting pathway information from a literature database comprising a biomedical publication;
      instructions for cross-referencing said pathway information to said candidate genes;
      instructions for ranking the biomedical publication and instructions to assign a ranking score to the pathway information extracted from a biomedical publication based on the ranking of the biomedical publication; and,
      instructions for viewing said cross-referenced information and said ranking score.

16. The data processing system of claim 15, wherein said executable instructions further comprise instructions for storing said pathway information and said cross-referenced information in a database.

17. A data processing system for identifying candidate genes from a plurality of DNA sequences, comprising:
   a processor; and,
   a memory coupled to the processor, wherein the memory has instructions for execution by the processor, the instructions comprising:
      instructions for clustering the plurality of DNA sequences based on the behavioral patterns of the DNA sequences as described by gene expression profile data;
      instructions for accessing and extracting pathway information from a literature database comprising a biomedical publication;
      instructions for cross-referencing said pathway information to said candidate genes;
      instructions for ranking the biomedical publication and instructions to assign a ranking score to the pathway information extracted from a biomedical publication based on the ranking of the biomedical publication; and,
   instructions for viewing said cross-referenced information and said ranking score.

* * * * *